(12) United States Patent
Brysch et al.

(10) Patent No.: US 11,007,192 B2
(45) Date of Patent: May 18, 2021

(54) USE OF 5-AMINO-2,3-DIHYDRO-1,4-PHTHALAZINEDIONE IN THE TREATMENT OF CHRONIC PROGRESSIVE MULTIPLE SCLEROSIS

(71) Applicant: METRIOPHARM AG, Zürich (CH)

(72) Inventors: Wolfgang Brysch, Berlin (DE); Astrid Kaiser, Berlin (DE); Claudia Van Laak, Berlin (DE); Beate Ludescher, Berlin (DE); Maliha Shah, Berlin (DE); Jörg Von Wegerer, Berlin (DE)

(73) Assignee: Metriopharm AG, Zürich (CH)

( * ) Notice: Subject to any disclaimer, the term of this patent is extended or adjusted under 35 U.S.C. 154(b) by 0 days.

(21) Appl. No.: 16/347,171

(22) PCT Filed: Nov. 6, 2017

(86) PCT No.: PCT/EP2017/001284
§ 371 (c)(1),
(2) Date: May 2, 2019

(87) PCT Pub. No.: WO2018/082814
PCT Pub. Date: May 11, 2018

(65) Prior Publication Data
US 2019/0358227 A1 Nov. 28, 2019

(30) Foreign Application Priority Data

Nov. 7, 2016 (EP) .................................. 16002355

(51) Int. Cl.
*A61K 31/502* (2006.01)
*A61K 9/00* (2006.01)
*A61P 25/28* (2006.01)

(52) U.S. Cl.
CPC .......... *A61K 31/502* (2013.01); *A61K 9/0053* (2013.01); *A61P 25/28* (2018.01)

(58) Field of Classification Search
CPC ...... A61K 31/502; A61K 9/0053; A61P 25/28
(Continued)

(56) References Cited

U.S. PATENT DOCUMENTS 8,772,294 B2 * 7/2014 Breu ....................... A61P 19/02
514/248
9,079,863 B2 * 7/2015 Breu ..................... C07D 237/32
(Continued)

FOREIGN PATENT DOCUMENTS

WO WO 2004/041169 A2 5/2004
WO WO 2007/018546 A1 2/2007
(Continued)

OTHER PUBLICATIONS

Qiang W. et al., Monosodium luminol (GVT), "A modular of activated microglia, is a potential treatment for neurodegenerative diseases", Abstracts of the Annual Meeting of the Society for Neuroscience, Society for Neuroscience, US, vol. 38, Jan. 1, 2008 (Jan. 1, 2008), XP009193958.
(Continued)

*Primary Examiner* — Kristin A Vajda
(74) *Attorney, Agent, or Firm* — Haug Partners LLP

(57) ABSTRACT

The invention relates to 5-amino-2,3-dihydro-1,4-phthalazinedione or related compounds, compositions or combinations thereof, for use in the treatment of chronic progressive multiple sclerosis, in particular primary and secondary progressive multiple sclerosis. The invention in particular relates to the use of 5-amino-2,3-dihydro-1,4-phthalazinedione sodium salt for said purposes.

11 Claims, 7 Drawing Sheets

Figure 1:
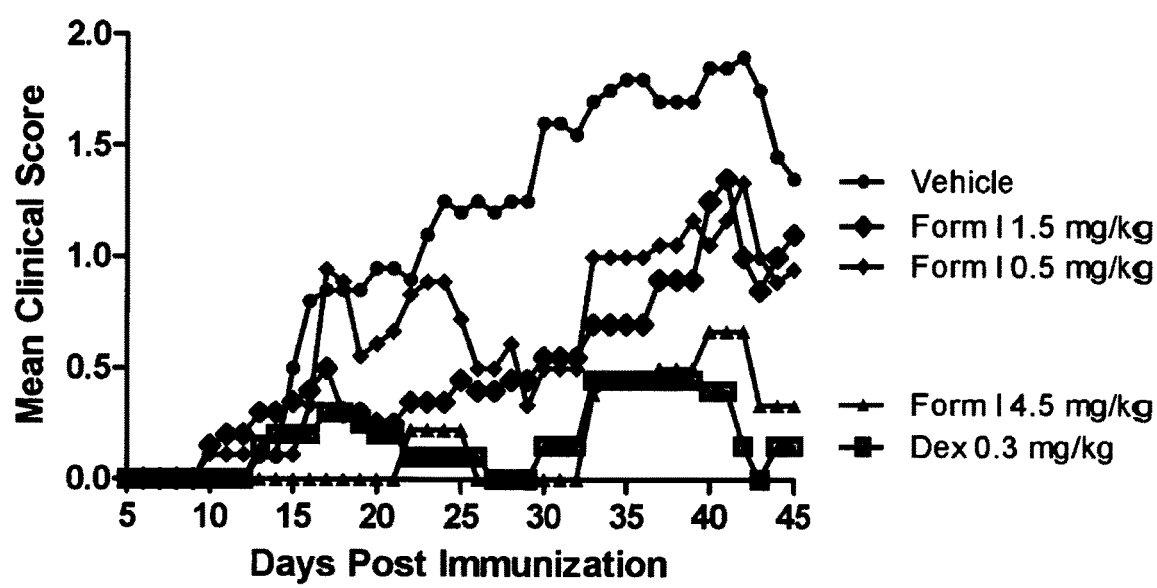

(58) Field of Classification Search
USPC .......................................................... 514/248
See application file for complete search history.

(56) References Cited

U.S. PATENT DOCUMENTS 10,258,620 B2 * 4/2019 Martin .................... A61P 37/02
2014/0303169 A1 10/2014 Breu et al.

FOREIGN PATENT DOCUMENTS

WO     WO 2010/082858 A2    7/2010
WO     WO 2016/096143 A1    6/2016

OTHER PUBLICATIONS

Fitzner Dirk et al., "Chronic Progressive Multiple Sclerosis—Pathogenesis of Neurodegeneration and Therapeutic Strategics", Current Neuropharmacology, vol. 8, No. 3, Sep. 2010 (Sep. 2010), pp. 305-315, XP002768833.
International Search Reportand Written Opinion dated Feb. 6, 2018 in corresponding International Application No. PCT/EP2017/001284.

* cited by examiner

USE OF 5-AMINO-2,3-DIHYDRO-1,4-PHTHALAZINEDIONE IN THE TREATMENT OF CHRONIC PROGRESSIVE MULTIPLE SCLEROSIS

CROSS-REFERENCE TO RELATED APPLICATIONS

This application is the National Stage entry under 35 U.S.C. § 371 of International Application No. PCT/EP2017/001284 filed on Nov. 6, 2017, published on May 11, 2018 under Publication Number WO 2018/082814, which claims the benefit of priority under 35 U.S.C. § 119 of European Patent Application Number 16002355.2 filed Nov. 7, 2016, the entireties of which are herein incorporated by reference.

The present invention relates to the use of 5-amino-2,3-dihydro-1,4-phthalazinedione or related compounds, including compositions and combinations containing 5-amino-2,3-dihydro-1,4-phthalazinedione or a related compound, in the treatment of chronic progressive courses of multiple sclerosis, in particular in the treatment of primary and secondary progressive multiple sclerosis.

The invention in particular relates to the use of 5-amino-2,3-dihydro-1,4-phthalazinedione sodium salt for said purposes.

BACKGROUND OF THE INVENTION

Multiple sclerosis (MS) is a generic term for the most frequent demyelinating disease of the central nervous system (CNS) in humans. The disease pattern is highly variable among patients. There are, however, two main variants that differ widely in their pathophysiology and their clinical manifestation. The first variant is relapsing-remitting multiple sclerosis (RRMS) which accounts for roughly 80% of all incidences, and the second variant are the chronic progressive forms of multiple sclerosis which are subdivided into primary progressive multiple sclerosis (PPMS) and secondary progressive multiple sclerosis (SPMS). In the International Statistical Classification of Diseases and Related Health Problems $10^{th}$ Revision (ICD-10-GM, German Modification, Version 2017, DIMDI 23 Sep. 2016) RRMS, PPMS and SPMS are classified as G35.1, G35.2 and G35.3, respectively. PPMS accounts for approximately 10 to 20% of all MS cases. There is an ongoing controversy whether RRMS and PPMS/SPMS are actually two different diseases that only coincidentally may become manifest together sharing a number of common pathophysiological features but are clearly differing in others.

RRMS is characterized by the incidence of unpredictable acute exacerbations (relapses) in the disease course, followed by phases of recovery to the previous base disease level, often of full recovery (remission). The intervals between relapses usually become shorter the longer a person is suffering from this disease. In most cases RRMS starts with a clinically isolated syndrome (CIS). A CIS represents an attack in one organ system probably due to demyelination. 30 to 70% of persons experiencing a CIS attack later develop MS.

PPMS is characterized clinically by the accumulation of neurological disability without unequivocal recovery (as reviewed by Pérez Cerdá et al., 2016, Multiple Sclerosis and Demyelinating Disorders 1:9). The disease progress in PPMS is more insidious and subtle than in RRMS with clearly defined relapses. There is a characteristic neuronal atrophy due to Wallerian-like degeneration, caused by demyelination and neurodegenerative oxidative damage of the axon. The characteristic onset of clinical symptoms in PPMS patients is around 40 years of age. PPMS is disproportionally more frequent in relatively MS-resistant populations (Africans, Orientals) and disproportionally more frequent in men. Whilst in general the relation of women and men suffering from MS is about 3 to 1 the relation in PPMS is approximately 1 to 1. SPMS is diagnosed after a previous RRMS stops developing relapse periods over a minimum of 3 months and a continuous deterioration of the clinical symptoms occurs. The symptoms of SPMS are substantially the same as of PPMS, although they may differ quantitatively. Therefore, most clinicians regard SPMS and PPMS as the same disease, mainly differing whether there was a previous phase of RRMS or not. The age difference concerning the onset of RRMS and PPMS is typically about 10 years, however the switch from RRMS to SPMS occurs at approximately the same age as PPMS usually becomes manifest (as reviewed by Antel et al., 2012, Acta Neuropathol 123:627-638).

Clinically, the time to disability is not driven by the relapse rate, their frequency or severity in PPMS/SPMS. In PPMS/SPMS immunological studies conducted on blood or cerebrospinal fluid (CSF) samples from patients showed that the levels of adhesion molecules, cytokine expression and chemokine receptors in PPMS patients were comparable to those in healthy controls, in contrast to RRMS patients with pathophysiologically altered levels. Using antigen microarrays significantly different serum antibody signatures could be identified in RRMS and PPMS. In PPMS 46% of the significantly differently expressed antibodies were down-regulated compared to healthy controls, whereas in RRMS 96% of the differentially expressed antibodies were upregulated. In RRMS, a marked immune response against HSP 60 or HSP 70 could be observed that is lacking in PPMS or SPMS. Also the production of nitric oxide (the most important reactive nitrogen species leading to oxidative stress in cells) is elevated in PPMS patients. N-acetyl-aspartate (NA), an established marker of neuronal integrity, is markedly reduced in PPMS patients, compared to controls (cf. Antel et al., 2012). However, Matsushita et al. (PLOS ONE, April 2013, Vol 8(4):e61835) found distinct cytokine/chemokine alterations in CSF when comparing RRMS and PPMS. In PPMS, increased CCL4 (C—C motif chemokine 4 sometimes also referred to as macrophage inflammatory protein-1β) and CXCL10 (C-X-C motif chemokine 10 also known as interferon gamma-induced protein 10 or small-inducible cytokine B10) levels reflect an on-going low grade inflammation in the central nervous system whilst in RRMS, only a mild elevation of proinflammatory cytokines/chemokines was detectable at relapse.

Although there is a wide variability, the incidence of focal brain lesion types seems to be reduced in PPMS patients, compared to RRMS patients. In contrast, a comparatively higher lesion load in the spinal cord seems to be typical for PPMS and SPMS. Neuronal atrophy in the whole brain and the grey matter is significantly stronger in PPMS patients. Grey matter atrophy is a characteristic early feature in PPMS. The respective signals are stronger in magnetization transfer imaging, diffusion tensor imaging and proton magnetic resonance spectroscopy in PPMS patient. Actively demyelinating white matter lesions characterized by the presence of abundant macrophages with cytoplasmic early myelin degradation products at the lesion border are more frequently observed in RRMS than in PPMS patients. Vessels with perivascular inflammation in PPMS/SPMS lack leakage of the blood-brain barrier and/or expression of markers associated with increased endothelial permeability.

This is reflected in fewer gadolinium enhancing lesions (cf. Antel et al., 2012). The lesser degree of inflammation in PPMS/SPMS leads to a compartmentalization in the CNS, e.g. meningeal inflammatory aggregates (lymphatic follicles-like).

It could be shown that chronic oxidative stress in PPMS/SPMS causes mitochondrial injury in CNS neurons. In consequence, a deletion of mitochondrial DNA could be observed over time, a symptom that is also found in other classical neurodegenerative diseases. This brings about an increased energy deficiency and an amplification of the oxidative injury. In the long run the reserve capacity of the CNS is exhausted. An increasing iron accumulation has been observed with aging. These iron ions are released from the demyelinating lesions and contribute to further oxidative injury. A consequence of oxidative stress injury and neurodegeneration can be a microglial activation in PPMS/SPMS, which does not occur to this degree in RRMS (cf. Perez Cerda et al., 2016). The role of microglia in PPMS/SPMS, however, is still controversially discussed in literature. Remyelination of demyelinated axons regularly occurs in RRMS, thus reestablishing the functionality of the affected muscles. This corresponds with a remission period in the disease course. In PPMS/SPMS, however, remyelination does not occur or only incompletely. Hence, inflammation declines with disease duration while neurodegeneration proceeds. Therein the affected axons appear paler than the normally myelinated axons of the white matter due to the reduction in axons and thinner myelin sheaths. Completely myelinated lesions (shadow plaques) are relatively rare in PPMS/SPMS, accounting for only ca. 20% of the lesions (cf. Perez Cercla et al., 2016). Taken together, the reduced number of new inflammatory lesions, the increase in atrophy and diffuse white matter abnormalities indicate a dominance of neurodegenerative mechanisms in PPMS/SPMS (Antel et al., 2012). Inflammation, however, is significantly less marked in PPMS/SPMS, though the clinical appearance of the disease in the patient may be more severe. Oversimplified it could be said that RRMS symptoms are mainly inflammatory, while PPMS/SPMS symptoms are predominantly neurodegenerative. Thus, substantially different pathophysiological mechanisms are involved in both MS forms, consequently requiring different pharmacological therapy approaches. Therefore, it is comprehensible that mainly anti-inflammatory or immunosuppressive drugs effective in RRMS treatment show only poor or no results in PPMS/SPMS treatment.

Regarding the clinician's view PPMS/SPMS are mainly characterized by continuos growing disabilty in the course of the disease. The so called Expanded Disability Status Scale (EDSS)—originally introcuced by Kurtzke (Neurology 1983 November; 33(11):1444-52)—is commonly used as ordinal scale to rate the grade of neurologic impairment: e.g. an EDSS>6 means that at least a constant bilateral support—cane, crutch, or braces—is required to walk 20 meters without resting (EDSS 6.5). The mean annualized EDSS increase amounts to 0.25 points (0.5 in 2 years) in SPMS patients and to 0.35 points in PPMS patients (Stellmann et al., PLOS ONE, March 2014, Vol. 9(3):e92761), however in the single patient the smallest EDSS grade unit is 0.5 points.

Only one drug has been recently approved for the treatment of PPMS. The anti-CD-20 monoclonal antibody ocrelizumab is directed against B cells. It shows moderate success, but has strong immunosuppressive actions triggering the well-known unwanted side effects of immunosuppressive drugs. Otherwise, only medications for the treatment of symptoms are prescribed. Conventional immunomodulatory therapies such as interferon beta and glatiramer acetate are ineffective. Thus, there is a huge medical need for a drug that effects a substantial improvement in the disease course of PPMS/SPMS. Surprisingly, it has been found that a systemic administration of 5-amino-2,3-dihydro-1,4-phthalazinedione sodium salt showed an excellent effect in PPMS/SPMS treatment, as will be specified in detail in Example 1.

According to the recommended therapy schemes for multiple sclerosis provided by the currently effective guideline (valid till September 2017) for diagnosis and therapy of multiple sclerosis published by the German Society for Neurology (Gold 2014; DGN: Leitlinien für Diagnostik and Therapie in der Neurologie) various drugs are recommended for the treatment of MS, depending on type, state and severity of the disease. Therapy suggestions include amongst others the administration of glatiramer acetate, interferon beta 1a, interferon beta 1 b, PEG interferon beta 1a, alemtuzumab, fingolimod, natalizumab, dimethyl fumarate, teriflunomide, mitoxantrone, cyclophosphamide and/or methylprednisolone, plasma separation and experimental methods. When it comes to SPMS without additional relapses the only therapy suggestions are the cytostatic drugs mitoxantrone and cyclophosphamide.

Although corticosteroids, as e.g. dexamethasone or methylprednisolone, have shown to be effective in a variety of disease models in animals and thus are used as positive controls (cf. Example 1, 2 and 3) they are not recommended to be used for long-term treatment in humans due to habituation and adverse reactions. Therefore, methylprednisolone is recommended for treating active states of multiple sclerosis within the scope of relapses only. It is not recommended to treat PPMS/SPMS.

Mitoxantrone is an immunosuppressive drug with a number of serious side effects, in particular bone marrow suppression and thus a lot of contraindications including amongst others viral and bacterial infections, heart diseases, insufficient performance of liver or kidneys, neutropenia and so on. Furthermore mitoxantrone is not allowed during pregnancy and breastfeeding, administration should even be stopped by both father and mother at least 6 months before procreation. Apart from that it often leads to infertility in both men and women. Due to this very unfavourable risk profile a maximum lifetime dosage has been established for mitoxantrone. The drug shall also not be administered in late/severe forms of the disease (EDSS>6) thereby withdrawing even this disadvantageous therapy from those patients. Mitoxantrone also has a negative impact on the efficacy of vaccines. Mitoxantrone has to be administered intravenously thus requiring an at least ambulant treatment.

Cyclophosphamide might be used in single cases of severe disease courses when no other treatment—including mitoxantrone—showed any stabilizing or at least decelerating effect. Cyclophosphamide is currently not approved for the treatment of MS, but used in individualized treatments. Adverse reactions and contraindications are comparable to those described for mitoxantrone above.

Both mitoxantrone and cyclophosphamide show only limited efficacy in decelerating the progression of the disease and thus the progression of inabilities in SPMS. There was no improvement shown in PPMS patients. Moreover, neither Gold (2014) nor further relevant guidances (Birnbaum 2013: Multiple Sclerosis: Clinician's Guide to Diagnosis and Treamtment, $2^{nd}$ ed, OANL; Willis 2016: BMJ Best Practice: Mulitiple sclerosis, last updated 26Jan. 2016) provide any therapy suggestions for PPMS.

5-amino-2,3-dihydro-1,4-phthalazinedione belongs to the pharmaceutical class of the phthalazinediones. Compounds of this class are known for their beneficial anti-inflammatory actions. 5-amino-2,3-dihydro-1,4-phthalazinedione is also well known under the names 3-aminophthalhydrazide and luminol. Luminol became known for its chemiluminescent properties. It is widely applied in diagnostic assays as a detection means and in forensic medicine, for example for tracing blood spots. In medicine, 5-amino-2,3-dihydro-1,4-phthalazinedione has been developed in the form of a sodium salt. Its use has been described for a broad range of acute and chronic inflammatory disorders, including amongst others acute infections of bacterial and viral origin, particularly of the intestinal tract, hepatitis B and C, gastroenteritis, inflammations such as prostatitis, endometriosis, throat inflammation, bronchial asthma, pneumonia, periodontitis, pyelonephritis and autoimmune diseases such as Crohn's disease, ulcerative colitis, lupus erythematosus and scleroderma. Further, there is still a long list of indications in scientific and patent literature in the treatment of which 5-amino-2,3-dihydro-1,4-phthalazinedione was allegedly tested or a beneficial use was at least suggested (cf. WO 2004/041169; WO 2007/018546; WO 2012/127441).

The use of 5-amino-2,3-dihydro-1,4-phthalazinedione or a related compound in the treatment of acute phases in MS, respectively RRMS has been suggested in WO 2011/107295 and WO 2010/082858, and has further been mentioned in WO 2016/096143, WO 2004/041169, U.S. Pat. No. 7,759,337 and WO 2007/018546 within the scope of long listings of inflammatory, respectively autoimmune diseases. Experimental evidence for an efficacy in MS (RRMS) is not provided therein. Trinitatskii (2003 Lechashchii Vrach, N6-C27) investigated the effect of 5-amino-2,3-dihydro-1,4-phthalazinedione sodium salt on various biochemical parameters, in particular specific cytokines and cytokine expressing receptors related thereto in patients with acute phase RRMS when administered as an add on therapy to a standard therapy. The standard therapy therein was composed as follows: mexidol (an antioxidant with a structure comparable to pyridoxin), nootropics, pyridoxine hydrochloride and a muscle relaxans (baclofen or detrusitol). Results, particularly the downregulation of TNFalpha, were at least promising, however these results were related to acute phase in the course of relapses only. Effective treatments of various indications are mostly referred to dosages of 100 mg 5-amino-2,3-dihydro-1,4-phthalazinedione sodium salt provided intramuscularly, orally or as suppository daily or each second day (cf. Trinitatskii 2003, WO 2010/082858, WO 2007/018546, WO 2016/096143). 5-amino-2,3-dihydro-1,4-phthalazinedione sodium salt is known as an active substance with a great immunomodulatory and anti-inflammatory potential. RRMS symptoms are mainly inflammatory, however PPMS and SPMS are based on different mechanisms as outlined above. In a poster presentation Qiang et al. (Neuroscience, Nov. 17, 2008, Program #/Poster #: 312.3) suggest that 5-amino-2,3-dihydro-1,4-phthalazinedione sodium salt might be able to prevent neuronal damage in neurodegenerative diseases which are associated with accumulation of various abnormal proteins if administered in low concentrations in vitro. However, if 5-amino-2,3-dihydro-1,4-phthalazinedione sodium salt was administered in higher concentrations apoptosis was activated, thus leading to a contrary effect.

An effective treatment of PPMS/SPMS using 5-amino-2,3-dihydro-1,4-phthalazinedione or a related compound, however, hasn't been described yet, neither as standalone nor in combination with other therapy approaches.

SUMMARY OF THE INVENTION

An effective treatment of PPMS/SPMS is a treatment that either completely cures the disease, stops the increase of disability in the course of the disease or at least significantly decelerates the increase of disability in the course of the disease. An effective treatment of PPMS/SPMS is thus generally associated with a substantial improvement in the disease course. As there is a huge medical need for a drug that effects a substantial improvement in the disease course of PPMS/SPMS, it was the task of this invention to provide such a drug.

A drug that effects a substantial improvement in the disease course of PPMS/SPMS may still vary in effectiveness depending on dosage, administration form and frequency. Thus, further tasks of this invention were to provide dosage forms and pharmaceutical forms, as well as treatment regimens allowing greater effectiveness of a drug administered for substantial improvement in the disease course of PPMS/SPMS.

Further, it was the task of this invention to provide a method of treatment for PPMS/SPMS.

Surprisingly, it has been found within the scope of an animal model mimicking PPMS (cf. Example 1) that a systemic administration of 5-amino-2,3-dihydro-1,4-phthalazinedione sodium salt showed an excellent effect on the disease course, in particular the dose of 4.5 mg/kg, which was higher than the doses that were usually effective in other experimental animal models (cf. Examples 2 and 3). These results implicate that 5-amino-2,3-dihydro-1,4-phthalazinedione or related compounds are effective in the treatment of PPMS/SPMS, in particular if applied in higher doses as has been shown effective for other indications.

Hence this invention refers to 5-amino-2,3-dihydro-1,4-phthalazinedione or related compounds for use in the treatment of chronic progressive forms of multiple sclerosis, in particular in the treatment of primary and secondary progressive multiple sclerosis, i.e. PPMS and SPMS. In particular the invention refers to 5-amino-2,3-dihydro-1,4-phthalazinedione sodium salt for said use.

The present invention also relates to the use of compositions and combinations containing 5-amino-2,3-dihydro-1,4-phthalazinedione or related compounds in the treatment of chronic progressive courses of multiple sclerosis, in particular in the treatment of primary and secondary progressive multiple sclerosis. The invention further refers to 5-amino-2,3-dihydro-1,4-phthalazinedione or related compounds for the treatment of PPMS/SPMS administered according to specific treatment regimes, in particular the invention refers to 5-amino-2,3-dihydro-1,4-phthalazinedione sodium salt for said use. The invention also refers to a method of treating PPMS/SPMS characterized by the administration of 5-amino-2,3-dihydro-1,4-phthalazinedione or related compounds to a subject in need thereof, preferably the administration of 5-amino-2,3-dihydro-1,4-phthalazinedione sodium salt.

While most conventional drugs used in the treatment of multiple sclerosis have serious adverse reactions, or are at least problematic in long-term treatment, 5-amino-2,3-dihydro-1,4-phthalazinedione or related compounds are well tolerated and have a high safety margin in respect to administered dosages. In addition to the many serious adverse reaction related to immunosuppressive drugs used to treat SPMS, as e.g. mitoxantrone or cyclophosphamide, these drugs also have very long biological half-lives illustrated in days or weeks. In contrast, 5-amino-2,3-dihydro-1,4-phthalazinedione or its related compounds as laid out below have a half-life of several hours, in detail depending on compound, dosage and formulation, however staying far away from days to weeks. Immunomodulatory drugs used in the treatment of multiple sclerosis and in particular the cytostatic drugs used in the treatment of SPMS require close monitoring of the patients due to their high toxic, teratogenic and carcinogenetic potential. 5-amino-2,3-dihydro-1,4-phthalazinedione or related compounds offer the possibility to pharmaceutically treat PPMS, a disease for which so far no effective treatment is available. 5-amino-2,3-dihydro-1,4-phthalazinedione or related compounds have been shown in other diseases to be effective when taken orally, thus providing an advantage compared to existing therapies, e.g. mitoxantrone and cyclophosphamide, which have to be administered via injections. Patient compliance is therefore expected to improve. 5-amino-2,3-dihydro-1,4-phthalazinedione and its related compounds are small molecules. Hence production costs are much lower than is the case e.g. for biologicals and cytostatic drugs.

DETAILED DESCRIPTION OF THE INVENTION

Definitions

Unless otherwise stated, any technical or scientific term used in the present invention has the meaning that a man skilled in the relevant technical art will attribute to them. In the sense of the present patent application the terms "medicine" and "medical" comprise human as well as veterinary medicine.

According to the application the terms "drug substance", "active substance", "active agent", "active ingredient" or "active pharmaceutical ingredient" (API) refer to 5-amino-2,3-dihydro-1,4-phthalazinedione or compounds related thereto, if not stated otherwise.

The terms "composition" or "pharmaceutical composition" comprise at least one active ingredient in any pharmacologically acceptable defined dosage and dosage form together with at least one pharmaceutically acceptable excipient, as well as all agents that are generated from the ingredients as outlined below directly or indirectly as a combination, accumulation, complex or crystal, or as a consequence of other reactions or interactions, as well as optionally at least one further pharmaceutical drug, as listed below.

The term "excipient" is used in this application to describe any component of a pharmaceutical composition apart of the active principle. The selection of suitable excipients depends on a variety of factors, such as the dosage form, the dosage, the desired solubility and stability of the composition.

The terms "effect", "therapeutic effect", "action", "therapeutic action", "efficacy" and "effectiveness" in regard to the substance of the invention or any other active substance mentioned in the description refers to causally occurring beneficial consequences in the organism to which said substance has been administered before.

According to the invention the terms "effective amount" and "therapeutically effective amount" refer to an amount of the substance of the invention that is sufficiently large to cause a desired beneficial effect in a subject in need of such a treatment.

The terms "treatment" and "therapy" comprise the administration of at least the substance of the invention, alone or in combination with at least one further pharmaceutical drug, independently of the chronological order of the administration. Such an administration is intended to substantially improve the disease course of PPMS/SPMS by either completely curing the disease or by stopping or decelerating the increase of disability during the course of the disease.

The terms "subject" and "patient" comprise individuals suffering from disease symptoms or disabilities related to PPMS/SPMS wherein the diagnosis PPMS or SPMS is either approved or suspected. Individuals are mammals, in particular humans.

Dosage and Administration:

The effective dosage of the active ingredient may vary depending on the particular compounds and compositions employed, the mode of administration, the condition being treated and the severity of the condition being treated.

Experimental animal models, e.g. on rheumatoid arthritis and LPS-induced cytokine response (Example 2 and 3), showed effective dosages of 5-amino-2,3-dihydro-1,4-phthalazinedione sodium salt within the range of 0.5 to 1 mg/kg per day when applied intraperitoneally (i.p.). Contrary to examples 2 and 3, in the experimental model for PPMS (Example 1) the most effective dose was 4.5 mg/kg. However, there was a slight tendency for improvement in the smaller dose groups as well. Effective dosages in human patients have been mostly described varying from 50 mg to 100 mg independent of indication and administration method when applied daily (see above).

Hence, an effective dosage of 5-amino-2,3-dihydro-1,4-phthalazinediones or a related compound for treating PPMS/SPMS in a subject in need thereof lies between 50 mg and 1200 mg per day, preferably between 100 mg and 1000 mg, preferably between 200 and 800 mg, most preferably between 300 mg and 600 mg.

In one embodiment of the invention the active ingredient is to be administered one or more times daily over at least 2 weeks, preferably over at least 1 month, preferably over at least 3 months, preferably over at least 6 months, preferably for about 6 to about 12 months, most preferably over at least 12 months.

In another embodiment of the invention the active ingredient is to be administered each second day, each third day or once a week over at least 2 weeks, preferably over at least 1 month, preferably over at least 3 months, preferably over at least 6 months, preferably for about 6 to about 12 months, most preferably over at least 12 months.

Any suitable route of administration for 5-amino-2,3-dihydro-1,4-phthalazinedione or a related compound may be employed for providing a subject, in particular a mammal, especially a human with an effective dosage of 5-amino-2,3-dihydro-1,4-phthalazinedione or a related compound.

According to the invention 5-amino-2,3-dihydro-1,4-phthalazinedione or a related compound, a composition containing 5-amino-2,3-dihydro-1,4-phthalazinedione or a related compound or a composition containing 5-amino-2,3-dihydro-1,4-phthalazinedione or a related compound and at least one of the below mentioned combinational drugs for use in the treatment of PPMS/SPMS can be applied orally, parenterally, intravenously, intraarterially, intramuscularly, topically, transdermally, subcutaneously, intradermally, sublingually, intravaginally, rectally or nasally.

In one embodiment of the invention the active ingredient is to be administered in a first step to a subject in need thereof in an effective dosage whereas the effective dosage is regularly adapted based on diagnostic criteria, preferably the course of disability progression, most preferably disease progression as determined by EDSS scale. Therefore 5-amino-2,3-dihydro-1,4-phthalazinedione or a related compound is to be administered to a subject in need thereof one or more times daily, preferably two times daily over at least 12 months, preferably over at least 6 months, most preferably over at least 3 months using an effective dosage between 200 mg and 600 mg daily, preferably between 300 and 500 mg daily, most preferably 400 mg daily. In a particularly preferred embodiment of the invention the active substance is administered orally. In a second step the dosage administered is continued, increased or decreased based on diagnostic criteria as outlined below. The new dosage of the active ingredient is then again applied one or more times daily, preferably two times daily over at least 12 months, preferably over at least 6 months, most preferably over at least 3 months followed by a continued, increased or decreased dosage based on the diagnostic criteria.

Time between diagnostic rounds can increase over at least 6 months, more preferably over at least 12 months if no dosage adjustment is necessary and dose is continued.

Active substance dosage is increased if the EDSS value increased 0.5 points compared to treatment start or latest dosage adjustment, provided treatment start or latest dosage adjustment occurred not longer than 24 months before. Active substance dosage is increased if the EDSS value increased 1.0 points or more compared to treatment start or latest dosage adjustment, provided treatment start or latest dosage adjustment occurred not longer than 48 months before. Active substance dosage is continued if the EDSS value stayed unchanged compared to treatment start or latest dosage adjustment, provided treatment start or latest dosage adjustment occurred not longer than 24 months before. Active substance dosage is continued if the EDSS value decreased 0.5 or 1.0 points compared to treatment start or latest dosage adjustment, independent of when the treatment started or the latest dosage adjustment occurred. Active substance dosage is continued if the EDSS value increased a maximum of 0.5 points compared to treatment start or latest dosage adjustment, provided treatment start or latest dosage adjustment occurred more than 24 months before. Active substance dosage is continued if the EDSS value decreased 1.5 points compared to treatment start or latest dosage adjustment, provided treatment start or latest dosage adjustment occurred longer than 12 months before. Active substance dosage is decreased if the EDSS value decreased 1.5 points compared to treatment start or latest dosage adjustment, provided treatment start or latest dosage adjustment occurred not longer than 12 months before. Active substance dosage is decreased if the EDSS value decreased 2.0 points or more compared to treatment start or latest dosage adjustment, independent of when the treatment started or the latest dosage adjustment occurred. Active substance dosage is decreased if the EDSS value stayed unchanged compared to treatment start or latest dosage adjustment, provided treatment start or latest dosage adjustment occurred longer than 24 months before.

A treatment regimen according to the invention is described in Example 4.

In another embodiment of the invention the active ingredient is administered to a subject in need thereof using a treatment regimen characterized by the more frequent administration of a higher dosage, followed by the less frequent administration of a lower dosage, followed by a period without administration of the active substance. Therefore 5-amino-2,3-dihydro-1,4-phthalazinedione or a related compound is to be administered to a subject in need thereof two or more times daily, preferably two times daily over at least 1 week, preferably over at least 2 weeks, most preferably over at least 1 month using an effective dosage between 300 mg and 1200 mg daily, preferably between 400 mg and 1000 mg daily, most preferably 600 mg daily, subsequently followed by a period where the active substance is administered daily or each second or third day, preferably once daily over at least 2 weeks, preferably over at least 1 month, most preferably over at least 2 months using an effective dosage between 50 mg and 600 mg daily, preferably between 100 mg and 400 mg daily, most preferably 200 mg daily, subsequently followed by period of at least 2 weeks, preferably over at least 1 month, most preferably over at least 2 months where no active substance is administered, wherein after the period without administration of active substance the treatment regimen starts again. Within the course of this treatment regimen the active substance can be administered parenterally or orally, preferably the less frequent lower dose is administered orally, most preferably both the more frequently administered higher dose and the less frequently administered lower dose are administered orally.

In a further variant of this treatment regimen one, two or three single high dose shots between 300 mg and 600 mg per injection are administered parenterally within one day prior to the orally administered more frequent higher dose and the less frequent lower dose periods. Such a treatment regimen is described in Example 4 as well.

Preferred oral formulations for use in the treatment of PPMS/SPMS are capsules or tablets containing 5-amino-2,3-dihydro-1,4-phthalazinedione or a related compound in an amount of 50 mg, 100 mg, 150 mg, 200 mg, 300 mg, 400 mg, 500 mg or 600 mg, preferably 100 mg, 150 mg, 200 mg, 300 mg or 400 mg, most preferably 150 mg.

Compound Variants (Related Compounds):

To ensure a better solubility and bioavailability pharmaceutically acceptable salts of 5-amino-2,3-dihydro-1,4-phthalazinedione are used. Sodium, potassium and lithium salts have been described for therapeutic applications (cf. WO 2010/082858). Crystal structures for lithium, sodium, potassium, rubidium and cesium salts were described in Guzei et al. (2013, Journal of Coordination Chemistry 66, 3722-3739). Thus the present patent application refers also to the use of all pharmaceutically acceptable salts of 5-amino-2,3-dihydro-1,4-phthalazinedione and related compounds. 5-amino-2,3-dihydro-1,4-phthalazinedione is often used as a hydrate, for example as sodium salt dihydrate. Thus the present patent application refers also to the use of all hydrates and other solvates of 5-amino-2,3-dihydro-1,4-phthalazinedione and its pharmaceutically acceptable salts. 5-amino-2,3-dihydro-1,4-phthalazinedione, its derivatives or pharmaceutically acceptable salts may build complexes with suitable ligands. Thus, the present patent application refers also to such complexes.

In order to ensure a reproducible and standardized API production and to provide improved stability features of an active agent anhydrous formulations are often preferred. Anhydrate forms of 5-amino-2,3-dihydro-1,4-phthalazinedione sodium salt have been described as crystalline polymorphs in WO 2011/107295 (Form I, Form II) and WO 2016/096143 (Form III). These crystalline polymorphs are virtually free from phase impurities and were characterized by means of X-ray powder diffraction. This method yields a set of characteristic d-values indicating interplanar spacings and of the corresponding 2-theta (2θ) angles under which Bragg reflections occur. Additionally, the relative intensities (upon normalization to the respectively highest peak as 100%) of the reflections are indicated therein. This yields a unique and unambiguous fingerprint of the respective polymorphs.

For Form I the following values were determined:
d values: 13.5; 6.9; 5.2; 4.6; 3.9; 3.5; 3.4; 3.3; 3.1; 3.0 and/or
2-theta values: 6.5; 12.7; 16.9; 19.3; 22.8; 25.8; 26.6; 27.2; 28.7; 30.3.

Form II is characterized by the following values:
d values: 12.9; 7.9; 7.1; 6.5; 5.3; 4.0; 3.7; 3.6; 3.3; 3.2 and/or
2-theta values: 6.8; 11.2; 12.5; 13.7; 16.7; 22.4; 24.3; 24.9; 27.2; 27.8.

Form III yielded the following values:
d values: 13.131; 7.987; 7.186; 6.566; 6.512; 5.372; 3.994; 3.662; 3.406; 3.288; 3.283; 3.222; 3.215; 3.127; 2.889 and/or
2-theta values: 6.73; 11.07; 12.31; 13.48; 13.59; 16.49; 22.24; 24.29; 26.14; 27.10; 27.14; 27.67; 27.72; 28.52; 30.93.

Thus the present patent application refers also to the use of all crystalline forms and polymorphs thereof of 5-amino-2,3-dihydro-1,4-phthalazinedione and its pharmaceutically acceptable salts.

Similar therapeutic effects are known for a variety of phthalazinediones, respectively of derivatives of 5-amino-2,3-dihydro-1,4-phthalazinedione and its pharmaceutically acceptable salts. An example is 6-amino-2,3-dihydrophthalazine-1,4-dione (isoluminol). An overview of suitable phthalazinediones is given in WO 2007/018546. It is reasonable to assume that these compounds show comparable effects when being used for the therapeutic applications according to the invention.

Tautomerism relates to a rapid intraconversion of organic compounds in which a hydrogen atom or proton formally migrates inside the compound. This is accompanied by a switch of a single bond and adjacent double bond. The single forms are called tautomers. For example, keto-enol tautomerism occurs in 5-amino-2,3-dihydro-1,4-phthalazinedione. Thus, the present patent application refers also to the use of all tautomers of 5-amino-2,3-dihydro-1,4-phthalazinedione and its pharmaceutically acceptable salts.

Isomer is a generic term for molecules with the same chemical formula but a different chemical structure. They can be differentiated into constitutional (structural) isomers (wherein an exchange of atoms or of a functional group occurs) and stereoisomers. Stereoisomers can be subdivided into enantiomers (non-superimposable mirror images of the same molecule) and diastereomers (the same molecule with a different configuration at one or more stereocenters). Diastereomers can be subdivided into cis/trans isomers (referring to the relative orientation of functional groups within a molecule) and on the other hand conformers (rotation about formally single bonds) and rotamers (different rotational positioning about a single bond). An example for a constitutional isomer of 5-amino-2,3-dihydro-1,4-phthalazinedione is 6-amino-2,3-dihydrophthalazine-1,4-dione (isoluminol). Stereoisomers may occur in phthalazinedione derivatives. Thus, the present patent application refers also to the use of all isomers of 5-amino-2,3-dihydro-1,4-phthalazinedione, its derivatives and pharmaceutically acceptable salts.

For some applications it may be desirable that isotopically enriched forms of the compounds of the invention are used, e.g. for diagnostic purposes. Thus, the present patent application refers also to such isotopically enriched forms of the compounds of the invention.

From a pharmacokinetic point of view or for a production rationale it may be preferable to use a prodrug as a dosage form. A prodrug is administered in a pharmacologically inactive form and is metabolically converted into the active Form inside the body. This conversion may occur systemically or locally. Thus the present patent application refers also to prodrugs of the compounds of the invention.

As used throughout the present application the term "5-amino-2,3-dihydro-1,4-phthalazinedione" shall encompass all the aforementioned molecular variants of 5-amino-2,3-dihydro-1,4-phthalazinedione, unless otherwise stated.

Pharmaceutical Composition:

The present application refers likewise to a pharmaceutical composition for use in the treatment of PPMS or SPMS, wherein said composition contains at least one of 5-amino-2,3-dihydro-1,4-phthalazinedione or any of aforementioned molecular variants of this compound and a carrier. Eligible carriers are all carriers known in the art and combinations thereof. In solid dosage forms they can be for example plant and animal fats, waxes, paraffins, starch, tragacanth, cellulose derivatives, polyethylene glycols, silicones, bentonites, silica, talcum, zinc oxide. For liquid dosage forms and emulsions suitable carriers are for example solvents, solubilizing agents, emulsifiers such as water, ethanol, isopropanol, ethyl carbonate, ethyl acetate, benzyl alcohol, benzyl benzoate, propylene glycol, 1,3-butyl glycol, cotton seed oil, peanut oil, olive oil, castor oil, sesame oil, glycerol fatty acid esters, polyethyl glycols, fatty acid esters of sorbitan. Suspensions may use carriers known in the art such as diluents (e.g. water, ethanol or propylene glycol), ethoxylized isostearyl alcohols, polyoxyethylene and polyoxyethylene sorbitan esters, microcrystalline cellulose, bentonites, agar agar, tragacanth.

The present application refers likewise to a composition for use in the treatment of PPMS or SPMS, wherein said composition contains at least one of 5-amino-2,3-dihydro-1,4-phthalazinedione or any of aforementioned molecular variants of this compound, a carrier and at least one excipient selected from a group comprising penetration enhancers; binding agents; solvents; solubilizing agents; buffers; preservatives; antioxidants; coatings; colorants; flavoring substances; aromatic substances; sweeteners; thickening agents; disintegrants; glidants; lubricants; emulsifiers; stabilizers; diluents; anti-caking agents (antiadherents); sorbents and opacifiers.

Permeation enhancers are often used in topical dosage forms. Suitable permeation enhancers comprise all pharmaceutically acceptable permeation enhancers known in the art, such as, without being limiting, azones such as laurocapran, 1-dodecylazacycloheptan-2-one; sulphoxides such as dimethylsulphoxide, DMAC, DMF; pyrrolidones such as 2-pyrrolidone, NI-methyl-2-pyrrolidone; alcohols such as ethanol, 1,2-propandiol or decanol; glycols such as propylene glycol, diethylene glycol, tetraethylene glycol; fatty acids such as oleic acid, lauric acid, sodium lauryl sulfate, myristic acid, isopropyl myristic acid, capric acid; nonic surfactants such as polyoxyethylene-2-oleyl ether, polyoxyethylene-2-stearyl ether; terpenes; terpenoids; oxazolidinones; urea; ceramide analogs, azone analogs, menthol derivatives, etherified derivatives, esterified derivatives, transkarbams, carbamate salts, TXA derivatives, DDAIP (dodecyl 2-(dimethylamino)propanoate), DDAK, natural essential oils (all of them listed in Chen et al. (2014) Asian J. Pharm. Sc. 9, 51-64); citric acid esters such as triethyl citrate; hydrophobin polypeptides; alpha-bisabolol; dimethyl isosorbide (Arlasove® DMI); ethoxydiglycol. Preferred is 1,2-propandiol.

The term binding agents refers to substances that bind powders or glue them together, rendering them cohesive through granule formation. They serve as a "glue" of the formulation. Binding agents increase the cohesive strength of the provided diluent or filler. Suitable binding agents are starch from wheat, corn, rice or potato, gelatine, naturally occurring sugars such as glucose, sucrose or beta-lactose, sweeteners from corn, natural and synthetic gums such as acacia, tragacanth or ammonium calcium alginate, sodium alginate, carboxymethyl cellulose, sodium carboxymethyl cellulose, hydroxypropyl carboxymethyl cellulose, polyethylene glycol, polyvinyl pyrrolidone, magnesium aluminium silicate, waxes and others. The percentage of the binding agent in the composition can range from 1-30% by weight, preferred 2-20% by weight, more preferred 3-10% by weight and most preferred 3-6% by weight.

Suitable solvents may be selected from the group comprising water, carbonated water, water for injection, water with isotonizing agents, saline, isotonic saline, alcohols, particularly ethyl and n-butyl alcohol, glycols, oleic and linoleic acid triglycerides, caprylic and capric acid, mono-, di- and triglycerides, polyoxyethylene caprylic and capric acid glycerides, propylene glycol fatty acid esters, low alkyl fatty acid esters, soy bean oil, propylene glycol laurate, polyoxyethylene (35) castor oil, polyoxyethylene glyceryl trioleate, ethyl butyrate, ethyl caprylate, ethyl oleate and mixtures thereof.

Suitable as surface-active solubilizing agents (solubilizers) are for example diethylene glycol monoethyl ester, polyethyl propylene glycol co-polymers, cyclodextrins such as α- and β-cyclodextrin, glyceryl monostearates such as Solutol HS 15 (Macrogol-15-hydroxystearate from BASF, PEG 660-15 hydroxystearates), sorbitan esters, polyoxyethylene glycol, polyoxyethylene sorbitanic acid esters, polyoxyethylene sorbitan monoleate, polyoxyethylene oxystearic acid triglyceride, polyvinyl alcohol, sodium dodecyl sulfate, (anionic) glyceryl monooleates etc.

Moreover, buffers or buffer solutions are preferred for liquid formulations, in particular for pharmaceutical liquid formulations. The terms buffer, buffer system and buffer solution, in particular of an aqueous solution, refer to the capacity of the system to resist a pH change by the addition of an acid or a base, or by dilution with a solvent. Preferred buffer systems may be selected from the group comprising formate, lactate, benzoic acid, oxalate, fumarate, aniline, acetate buffer, citrate buffer, glutamate buffer, phosphate buffer, succinate, pyridine, phthalate, histidine, MES (2-(N-morpholino) ethanesulfonic acid, maleic acid, cacodylate (dimethyl arsenate), carbonic acid, ADA (N-(2-acetamido) imino diacetic acid, PIPES (4-piperazine-bis-ethanesulfonic acid), BIS-TRIS propane (1,3-bis[tris(hydroxymethyl)mehylaminol] propane), ethylene diamine, ACES (2-[(amino-2-oxoethyl)amino]ethanesulfonic acid), imidazol, MOPS (3-(N-morphino)-propanesulfonic acid, diethyl malonic acid, TES (2-[tris(hydroxymethyl)-methyl]aminoethanesulfonic acid, HEPES (N-2-hydroxyethylpiperazine-N'-2-ethanesulfonic acid), as well as other buffers with a $pK_a$ between 3.8 and 7.7.

Preferred are carbonic acid buffers such as acetate buffer and dicarboxylic acid buffers such as fumarate, tartrate and phthalate as well as tricarboxylic acid buffers such as citrate.

A further group of preferred buffers are inorganic buffers such as sulfate hydroxide, borate hydroxide, carbonate hydroxide, oxalate hydroxide, calcium hydroxide and phosphate buffers. Another group of preferred buffers are nitrogen-containing puffers such as imidazol, diethylene diamine and piperazine. Furthermore preferred are sulfonic acid buffers such as TES, HEPES, ACES, PIPES, [(2-hydroxy-1,1-bis-(hydroxymethyl)ethypamino]-1-propanesulfonic acid (TAPS), 4-(2-hydroxyethyl)piperazine-1-propanesulfonic acid (EEPS), 4-morpholino-propanesulfonic acid (MOPS) and N,N-bis-(2-hydroxyethyl)-2-aminoethanesulfonic acid (BES). Another group of preferred buffers are glycine, glycyl-glycine, glycyl-glycyl-glycine, N,N-bis-(2-hydroxyethyl)glycine and N-[2-hydroxy-1,1-bis(hydroxymethyl)ethyl]glycine (tricine). Preferred are also amino acid buffers such as glycine, alanine, valine, leucine, isoleucine, serine, threonine, phenylalanine, tyrosine, tryptophan, lysine, arginine, histidine, aspartate, glutamate, asparagine, glutamine, cysteine, methionine, proline, 4-hydroxy proline, N,N,N-trimethyllysine, 3-methyl histidine, 5-hydroxy-lysine, o-phosphoserine, gamma-carboxyglutamate, [epsilon]-N-acetyl lysine, [omega]-N-methyl arginine, citrulline, ornithine and their derivatives.

Preservatives for liquid dosage forms or supplements can be used on demand. They may be selected from the group comprising sorbic acid, potassium sorbate, sodium sorbate, calcium sorbate, methyl paraben, ethyl paraben, methyl ethyl paraben, propyl paraben, benzoic acid, sodium benzoate, potassium benzoate, calcium benzoate, heptyl p-hydroxybenzoate, sodium methyl para-hydroxybenzoate, sodium ethyl para-hydroxybenzoate, sodium propyl para-hydroxybenzoate, benzyl alcohol, benzalkonium chloride, phenylethyl alcohols, cresols, cetylpyridinium chloride, chlorobutanol, thiomersal (sodium 2-(ethylmercurithio) benzoic acid), sulfur dioxide, sodium sulphite, sodium bisulphite, sodium metabisulphite, potassium metabisulphite, potassium sulphite, calcium sulphite, calcium hydrogen sulphite, potassium hydrogen sulphite, biphenyl, orthophenyl phenol, sodium orthophenyl phenol, thiabendazole, nisin, natamycin, formic acid, sodium formate, calcium formate, hexamine, formaldehyde, dimethyl dicarbonate, potassium nitrite, sodium nitrite, sodium nitrate, potassium nitrate, acetic acid, potassium acetate, sodium acetate, sodium diacetate, calcium acetate, ammonium acetate, dehydroacetic acid, sodium dehydroacetate, lactic acid, propionic acid, sodium propionate, calcium propionate, potassium propionate, boric acid, sodium tetraborate, carbon dioxide, malic acid, fumaric acid, lysozyme, copper-(II)-sulfate, chlorine, chlorine dioxide and other suitable substances or compositions known to the person skilled in the art.

The addition of antioxidants is particularly preferable in topical dosage forms. Suitable examples for antioxidants include sodium metabisulfite, alpha-tocopherol, ascorbic acid, maleic acid, sodium ascorbate, ascorbyl palmitate, butylated hydroxyanisol, butylated hydroxytoluol, fumaric acid or propyl gallate. Preferred is the use of sodium metabisulfite.

Tablets or pills are usually coated, i.e. the coating constitutes the outer layer. This can be a film coating, a sugar coating with saccharides and a compression coating. Pharmaceutically acceptable varnishes or waxes, HPMC, MC or HPC can be used. Such a coating may help to disguise the taste, to ease the swallowing or the identification. Often plasticizers and pigments are included in the coating.

Capsules normally have a gelatinous envelope that encloses the active substance. The specific composition and thickness of this gelatinous layer determines how fast absorption takes place after ingestion of the capsule. Of special interest are sustained release formulations, as known in the art.

Colorants are excipients that bestow a colonization to the composition of the drink, respectively the dosage form. These excipients can be food colorants. They can be adsorbed on a suitable adsorption means such as clay or aluminium oxide. The amount of the colorant may vary between 0.01 and 10% per weight of the composition, preferred between 0.05 and 6% per weight, more preferred between 0.1 and 4% per weight, most preferred between 0.1 and 1% per weight. Suitable food colorants are curcumin, riboflavin, riboflavin-5'-phosphate, tartrazine, alkanin, quinolione yellow WS, Fast Yellow AB, riboflavin-5'-sodium phosphate, yellow 2G, Sunset yellow FCF, orange GGN, cochineal, carminic acid, citrus red 2, carmoisine, amaranth, Ponceau 4R, Ponceau SX, Ponceau 6R, erythrosine, red 2G, Allura red AC, lndathrene blue RS, Patent blue V, indigo carmine, Brilliant blue FCF, chlorophylls and chlorophyllins, copper complexes of chlorophylls and chlorophyllins, Green S, Fast Green FCF, Plain caramel, Caustic sulphite caramel, ammonia caramel, sulphite ammonia caramel, Black PN, Carbon black, vegetable carbon, Brown FK, Brown HT, alpha-carotene, beta-carotene, gamma-carotene, annatto, bixin, norbixin, paprika oleoresin, capsanthin, capsorubin, lycopene, beta-apo-8'-carotenal, ethyl ester of beta-apo-8'-carotenic acid, flavoxanthin, lutein, cryptoxanthin, rubixanthin, violaxanthin, rhodoxanthin, canthaxanthin, zeaxanthin, citranaxanthin, astaxanthin, betanin, anthocyanins, saffron, calcium carbonate, titanium dioxide, iron oxides, iron hydroxides, aluminium, silver, gold, pigment rubine, tannin, orcein, ferrous gluconate, ferrous lactate.

Suitable aromatic and flavoring substances comprise above all essential oil that can be used for this purpose. In general, this term refers to volatile extracts from plants or parts of plants with the respective characteristic smell. They can be extracted from plants or parts of plants by steam distillation. Examples are: Essential oils, respectively aromatic substances from sage, cloves, chamomile, anise, star anise, thyme, tea tree, peppermint, mint oil, menthol, cineol, eucalyptus oil, mango, figs, lavender oil, chamomile blossoms, pine needles, cypress, oranges, rosewood, plum, currant, cherry, birch leaves, cinnamon, limes, grapefruit, tangerine, juniper, valerian, lemon balm, lemon grass, palmarosa, cranberry, pomegranate, rosemary, ginger, pineapple, guava, echinacea, ivy leave extract, blueberry, kaki, melons etc. or mixtures thereof, as well as mixtures of menthol, peppermint and star anise oil or menthol and cherry flavor.

These aromatic or flavoring substances can be included in the range of 0.0001 to 10% per weight (particularly in a composition), preferred 0.001 to 6% per weight, more preferred 0.001 to 4% per weight, most preferred 0.01 to 1% per weight, with regard to the total composition. Application- or single case-related it may be advantageous to use differing quantities.

Suitable sweeteners can be selected from the group comprising mannitol, glycerol, acesulfame potassium, aspartame, cyclamate, isomalt, isomaltitol, saccharin and its sodium, potassium and calcium salts, sucralose, alitame, thaumatin, glycyrrhizin, neohesperidine dihydrochalcone, steviol glycosides, neotame, aspartame-acesulfame salt, maltitol, maltitol syrup, lactitol, xylitol, erythritol.

Suitable thickening agents can be selected from the group comprising polyvinyl pyrrolidone, methyl cellulose, hydroxypropyl methyl cellulose, hydroxypropyl cellulose, dextrins, polydextrose, modified starch, alkaline modified starch, bleached starch, oxidized starch, enzyme-treated starch, monostarch phosphate, distarch phosphate esterified with sodium trimetaphosphate or phosphorus oxychloride, phosphate distarch phosphate, acetylated distarch phosphate, starch acetate esterified with acetic anhydride, starch acetate esterified with vinyl acetate, acetylated distarch adipate, acetylated distarch glycerol, distarch glycerin, hydroxy propyl starch, hydroxy propyl distarch glycerine, hydroxy propyl distarch phosphate, hydroxy propyl distarch glycerol, starch sodium octenyl succinate, acetylated oxidized starch, hydroxyethyl cellulose.

Suitable disintegrants can be selected from the group comprising starch, cold water-soluble starches such as carboxymethyl starch, cellulose derivatives such as methyl cellulose and sodium carboxymethyl cellulose, microcrystalline cellulose and cross-linked microcrystalline celluloses such as croscarmellose sodium, natural and synthetic gums such as guar, agar, karaya (Indian tragacanth), locust bean gum, tragacanth, clays such as bentonite, xanthan gum, alginates such as alginic acid and sodium alginate, foaming compositions a.o. Moisture expansion is supported by for example starch, cellulose derivatives, alginates, polysaccharides, dextrans, cross-linked polyvinyl pyrrolidone. The amount of the disintegrant in the composition may vary between 1 and 40% per weight, preferred between 3 and 20% per weight, most preferred between 5 and 10% per weight.

Glidants are materials that prevent a baking of the respective supplements and improve the flow characteristics of granulations so that the flow is smooth and constant. Suitable glidants comprise silicon dioxide, magnesium stearate, sodium stearate, starch and talcum. The amount of the glidant in the composition may vary between 0.01 and 10% per weight, preferred between 0.1 and 7% per weight, more preferred between 0.2 and 5% per weight, most preferred between 0.5 and 2% per weight.

The term lubricants refers to substances that are added to the dosage Form In order to facilitate tablets, granulates etc. to be released from the press mold or the outlet nozzle. They diminish friction or abrasion. Lubricants are usually added shortly before pressing, as they should be present on the surface of the granules and between them and the parts of the press mold. The amount of the lubricant in the composition may vary between 0.05 and 15% per weight, preferred between 0.2 and 5% per weight, more preferred between 0.3 and 3% per weight, most preferred between 0.3 and 1.5% per weight. Suitable lubricants are a.o. sodium oleate, metal stearates such as sodium stearate, calcium stearate, potassium stearate and magnesium stearate, stearic acid, sodium benzoate, sodium acetate, sodium chloride, boric acid, waxes having a high melting point, polyethylene glycol.

Emulsifiers can be selected for example from the following anionic and non-ionic emulsifiers: Anionic emulsifier waxes, cetyl alcohol, cetylstearyl alcohol, stearic acid, oleic acid, polyoxyethylene polyoxypropylene block polymers, addition products of 2 to 60 mol ethylene oxide to castor oil and/or hardened castor oil, wool wax oil (lanolin), sorbitan esters, polyoxyethylene alkyl esters, polyoxyethylene sorbitan fatty acid esters, polyoxyethene sorbitan monolaurate, polyoxyethene sorbitan monooleate, polyoxyethene sorbitan monopalmitate, polyoxyethene sorbitan monostearate, polyoxyethene sorbitan tristearate, polyoxyethene stearate, polyvinyl alcohol, metatartaric acid, calcium tartrate, alginic acid, sodium alginate, potassium alginate, ammonium alginate, calcium alginate, propane-1,2-diol alginate, carrageenan, processed eucheuma seaweed, locust bean gum, tragacanth, acacia gum, karaya gum, gellan gum, gum ghatti, glucomannane, pectin, amidated pectin, ammonium phosphatides, brominated vegetable oil, sucrose acetate isobutyrate, glycerol esters of wood rosins, disodium phosphate, trisodium diphosphate, tetrasodium diphosphate, dicalcium diphosphate, calcium dihydrogen diphosphate, sodium triphosphate, pentapotassium triphosphate, sodium polyphosphates, sodium calcium polyphosphate, calcium polyphosphates, ammonium polyphosphate, beta-cyclodextrin, powdered cellulose, methyl cellulose, ethyl cellulose, hydroxypropyl cellulose, hydroxypropyl methylcellulose, ethyl methyl cellulose, carboxymethyl cellulose, sodium carboxymethyl cellulose, ethyl hydroxyethyl cellulose, crosscarmellose, enzymically hydrolyzed carboxymethyl cellulose, mono- and diglycerides of fatty acids, glyceryl monostearate, glyceryl distearate, acetic acid esters of mono- and diglycerides of fatty acids, lactic acid esters of mono- and diglycerides of fatty acids, citric acid esters of mono- and diglycerides of fatty acids, tartaric acid esters of mono- and diglycerides of fatty acids, mono- and diacetyl tartaric acid esters of mono- and diglycerides of fatty acids, mixed acetic and tartaric acid esters of mono- and diglycerides of fatty acids, succinylated monoglycerides, sucrose esters of fatty acids, sucroglycerides, polyglycerol esters of fatty acids, polyglycerol polyricinoleate, propane-1,2-diol esters of fatty acids, propylene glycol esters of fatty acids, lactylated fatty acid esters of glycerol and propane-1, thermally oxidized soy bean oil interacted with mono- and diglycerides of fatty acids, dioctyl sodium suiphosuccinate, sodium stearoyl-2-lactylate, calcium stearoyl-2-lactylate, stearyl tartrate, stearyl citrate, sodium stearoyl fumarate, calcium stearoyl fumarate, stearyl tartrate, stearyl citrate, sodium stearoyl fumarate, calcium stearoyl fumarate, sodium laurylsulfate, ethoxylated mono- and diglycerides, methyl glucoside-coconut oil ester, sorbitan monostearate, sorbitan tristrearate, sorbitan monolaurate, sorbitan monooleate, sorbitan monopalmitate, sorbitan trioleate, calcium sodium polyphosphate, calcium polyphosphate, ammonium polyphosphate, cholic acid, choline salts, distarch glycerol, starch sodium octenyl succinate, acetylated oxidized starch. Preferred are glycerin monooleate, stearic acid, phospholipids such as lecithin.

Stabilizers are substances that can be added to prevent unwanted changes in other supplements. Though stabilizers are not real emulsifiers they may also contribute to the stability of emulsions. Suitable examples for stabilizers are oxystearin, xanthan gum, agar, oat gum, guar gum, tara gum, polyoxyethene stearate, aspartame-acesulfame salt, amylase, proteases, papain, bromelain, ficin, invertase, polydextrose, polyvinyl pyrrolidone, polyvinyl polypyrrolidone, triethyl citrate, maltitol, maltitol syrup.

Diluents or fillers are inactive substances added to drugs in order to handle minimal amounts of active agents. Examples for suitable diluents are water, mannitol, pregelatinized starch, starch, microcrystalline cellulose, powdered cellulose, silicified microcrystalline cellulose, dibasic calcium phosphate dihydrate, calcium phosphate, calcium carbonate, hydroxypropyl cellulose, hydroxyethyl cellulose, hydroxypropyl methylcellulose, polyethylene glycol, xanthum gum, gum arabic or any combination thereof.

Anti-caking agents (antiadherents) can be added to a supplement or a composition of supplements in order to prevent the formation of lumps and for easing packaging, transport, release from the at least one chamber of the dispensing cap and consumption. Suitable examples include tricalcium phosphate, powdered cellulose, magnesium stearate, sodium bicarbonate, sodium ferrocyanide, potassium ferrocyanide, calcium ferrocyanide, bone phosphate, sodium silicate, silicon dioxide, calcium silicate, magnesium trisilicate, talcum powder, sodium aluminosilicate, potassium aluminium silicate, calcium aluminosilicate, bentonite, aluminium silicate, stearic acid, polydimethyl siloxane.

Sorbents are materials that soak up oil from the water. Suitable examples include natural sorbents such as peat moss, sawdust, feathers, and anything else natural that contains carbon and synthetic sorbents such as polyethylene and nylon. Sorbents are used for tablet/capsule moistureproofing by limited fluid sorbing (taking up of a liquid or a gas either by adsorption or by adsorption) in a dry state.

Opacifiers are substances that render the drinkable liquid opaque, if desired. They must have a refractive index substantially different from the solvent, in most cases here water. At the same time they should be inert to the other components of the composition. Suitable examples include titanium dioxide, talc, calcium carbonate, behenic acid, cetyl alcohol, or mixtures thereof.

For the production of a dosage form as a 5-amino-2,3-dihydro-1,4-phthalazinedione containing suppository waxes with a low melting point as well as a mixture of fatty acid glycerides such as cocoa butter are first melted, then 5-amino-2,3-dihydro-1,4-phthalazinedione is homogenously dispersed under stirring or other mixing methods. The molten homogeneous mixture is then transferred to suitable molds and cooled down until solidification.

All of the aforementioned substances and classes of substances can be used as supplementary excipients according to the invention, alone or in any conceivable combination thereof.

Combinations:

5-amino-2,3-dihydro-1,4-phthalazinedione or a related compound can be used as monotherapy or can further be combined with at least one further active ingredient selected from a group comprising active ingredients used in the disease-modifying therapies for multiple sclerosis, in symptomatic therapies for multiple sclerosis and in the treatment of comorbidities.

Suitable examples for active ingredients used for disease modifying therapies for multiple sclerosis comprise beta interferons as e.g. IFN beta-1b, IFN beta-1a or PEG-IFN beta 1a, glatiramer acetate, fingolimod, teriflunomid, mitoxantrone, natalizumab, laquinimod, dimethyl fumarate, alemtuzumab, idebenone, ibudilast, ocrelizumab, methylprednisolone, cyclophosphamide, piracetam, pyridoxine hydrochloride, vitamin D and further immunomodulators, nootropics and antioxidants for use in the treatment of PPMS or SPMS.

Symptomatic therapy within the scope of multiple sclerosis might get necessary to treat for example spasms, tremor, gait impairments, fatigue or dysfunction of the bladder. Suitable examples for active ingredients used in symptomatic therapies for multiple sclerosis thus comprise gabapentin, carbamazepine, pregabalin, oxcarbazepine, clonazepam, baclofen, tizanidine, localized botulinum toxin injections, propranolol, primidone, eugeroics such as modafinil and armodafinil, methylphenidate, potassium channel blockers such as fampridine and dalfampridine, amantadine, solifenacin, darifenacin, tolterodine, fesoterodine, trospium and oxybutynin.

Comorbidities can result from impairments due to multiple sclerosis or are independent thereof. Thus 5-amino-2,3-dihydro-1,4-phthalazinedione or a related compound can further be combined with at least one further active ingredient selected from a group comprising steroidal and non-steroidal anti-inflammatory drugs; immunomodulators; immunostimulatory agents; immunosuppressive agents; cognitive enhancers, antidepressants and other mood modifying agents, agents to prevent loss of bone density, agents to prevent sleep apnea and sleep-modifying agents, agents to treat or prevent sexual dysfunction, agents to treat metabolic syndrome, agents to treat skin lesions such as pressure scores or intertrigo, antibiotics; anti-infective agents like antiviral agents; antifungal agents; antiprotozoal agents and anthelmintics; analgesics; local anesthetics; anticoagulants;

antiplatelet drugs; muscle relaxants and tonic agents for use in the treatment of PPMS or SPMS.

Suitable examples for such steroidal anti-inflammatory drugs comprise corticosteroids, glucocorticoids, cortisone, cortisone acetate, hydrocortisone, hydrocortisone acetate, dexamethasone, betamethasone, prednisone, prednisolone, methylprednisolone, deltasone, triamcinolone, tixocortol pivalate, mometasone, amcinonide, budesonide, desonide, fluociconide, fluocinolone, halcinonide, fluocortolone, hydrocortisone-17-valerate, halometasone, alclometasone dipropionate, betamethasone valerate, betamethasone dipropionate, prednicarbate, clobetasone-17-butyrate, clobetasol-17-propionate, fluocortolone caproate, fluocortolone pivalate, fluprednidene acetate, hydrocortisone-17-butyrate, hydrocortisone-17-aceponate, hydrocortisone-17-buteprate, ciclesonide, flunisolide, fluticasone furoate, fluticasone propionate, triamcinolone acetonide, beclomethasone dipropionate.

Suitable examples for such non-steroidal anti-inflammatory drugs (NSAIDs) comprise acetylsalicylic acid, salicylic acid and salicylates, acetaminophen (paracetamol), salsalate, diflunisal, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, nabumetone, piroxicam, meloxicam, tenoxicam, droxicam, lornoxicam, isoxicam, phenylbutazone, mefenamic acid, meclofenamic acid, flufenamic acid, tolfenamic acid, celexoxib, rofecoxib, valdecoxib, parecoxib, lumiracoxib, etoricoxib, firocoxib, nimesulide, clonixin, licofelone, H-harpagide, flunixin, tiaprofenic acid.

Suitable examples for such immunomodulators amongst others comprise thalidomide, lenalidomide, pomalidomide and apremilast.

Suitable examples for such antiviral drugs comprise ancriviroc, aplaviroc, cenicriviroc, enfuvirtide, maraviroc, vicriviroc, amantadine, rimantadine, pleconaril, idoxuridine, aciclovir, brivudine, famciclovir, penciclovir, sorivudine, valaciclovir, cidofovir, ganciclovir, valganciclovir, sofosbusvir, foscarnet, ribavirine, taribavirine, filibuvir, nesbuvir, tegobuvir, fosdevirine, favipiravir, merimepodib, asunaprevir, balapiravir, boceprevir, ciluprevir, danoprevir, daclatasvir, narlaprevir, telaprevir, simeprevir, vanipevir, rupintrivir, fomivirsen, amenamevir, alisporivir, bevirimate, letermovir, laninamavir, oseltamivir, peramivir, zanamivir.

Suitable examples for such immunostimulatory agents comprise interferons (α-, β-, γ-, τ-interferon), interleukins, CSF, PDGF, EGF, IGF, THF, levamisole, dimepranole, inosine. Suitable examples for such immunosuppressive drugs comprise the groups of glucocorticoids such as listed above; cytostatics such as alkylating agents (such as cyclophosphamide), antimetabolites such as methotrexate, azathioprine, mercaptopurine, fluorouracil, leflunomid, protein synthesis inhibitors and certain antibiotics such as dactinomycin, anthracyclines, mitomycin C, bleomycin and mithramycin, intercalating agents such as mitoxantrone; antibodies such as muromonab-CD3, rituximab, ustekinumab, alemtuzumab, natalizumab, basiliximab and daclizumab; drugs acting on immunophilins such as ciclosporin, tacrolimus and sirolimus, opioids, TNF binding proteins such as infliximab, etanercept, adalimumab; or curcumin, catechins, mycophenolic acid, fingolimod, myriocin and fumaric acid dimethyl esters.

Suitable examples for such cognitive enhancers comprise eugeroics such as armodafinil and modafinil; amphetamines such as dextroamphetamine and lisdexamfetamine; methamphetamine; racetams such as oxiracetam, piracetam, aniracetam, pramiracetam and phenylpiracetam; herbals such as Bacopa monnieri, *Panax ginseng* and *Ginkgo biloba*; Noopept (N-phenylacetyl-L-prolylglycine ethyl ester); xanthines such as caffeine; vitamin B6; vitamin B12; methylphenidate; and acetylcholinesterase inhibitors such as donepezil.

Suitable examples for such antidepressants and other mood modifying agents comprise tricyclic antidepressants such as desipramine, imipramine, amitriptyline and doxepine; tetracyclic antidepressants such as maprotiline and mirtazapine; selective serotonin re-uptake inhibitors such as sertraline, citalopram and fluoxetine; serotonin-norepinephrine reuptake inhibitors like e.g venlafaxine, milnaciprane and duloxetine; serotonin modulators and stimulators such as nefazodone, trazodone and vilazodone; norepinephrine reuptake inhibitors lik e.g. atomoxetine, reboxetine and viloxazine; tetracyclic antidepressants such as maprotiline and mirtazapine; and monoamine oxidase inhibitors such as selegiline, isocarboxazid, tranylcypromine, selegiline and phenelzine.

Suitable examples for such agents to prevent loss of bone density comprise bisphosphonates such as alendronate, risedronate sodium, ibandronate and zoledronate; selective estrogen receptor modulators such as raloxifene; parathyroid hormone such as teriparatide; vitamin D and mineral supplements such as calcium citrate.

Suitable examples for such sleep modifying agents comprise benzodiazepines such as temazepam, diazepam, alprazolam and oxazepam; baclofen; tizanidine; melatonin (e.g. Circadin®); and eugeroics such as armodafinil and modafinil. Eugeroics are also suitable examples for agents to prevent sleep apnea.

Suitable examples for such agents to treat or prevent sexual dysfunction comprise phosphodiesterase type 5 inhibitors such as sildenafil, tadalafil and vardenafil; yohimbine, L-arginine; and herbals such as *Panax ginseng, Lepidium meyenii* and *Crocus sativus*.

Suitable examples for such agents to treat metabolic syndrome comprise biguanide drugs such as metformin; sulfonylurea drugs such as glimepiride; insulin sensitizers such as pioglitazone; lipid lowering agents such as statins, niacin, fenofibrate and gemfibrozil; ACE inhibitors such as captopril, lisinopril and enalapril; angiotensin II receptor blockers such as irbesartan, losartan and valsartan; omega-3 polyunsaturated fatty acid; and antiplatelet agents as outlined in detail below.

Suitable examples for such agents to treat skin lesions such as pressure scores or intertrigo comprise topical treatments e.g. greer's goo (nystatin powder, hydrocortisone powder and zinc oxide paste), triple paste (contains petrolatum, zinc oxide paste, and aluminum acetate solution) and Desitin® paste (contains zinc oxide, petrolatum, cod liver oil and Lanolin) and antibacterial creams containing e.g. silver sulfadiazine or bactroban as active agent.

Suitable examples for such antibiotics comprise imipenem, meropenem, ertapenem, cephalosporins, aztreonam, penicillins such as penicillin G and penicillin V, piperacillin, mezlocillin, ampicillin, amoxicillin, flucloxacillin, methicillin, oxacillin, clavulanic acid, sulbactam, tazobactam, sultamicillin, fosfomycin, teicoplanin, vancomycin, bacitracin, colistin, gramicidin, polymyxin B, tyrothricin, teixobactin, fosmidomycin, amikacin, gentamicin, kanamycin, neomycin, netilmicin, streptomycin, tobramycin, chloramphenicol, fusidic acid, cethromycin, narbomycin, telithromycin, clindamycin, lincomycin, daptomycin, dalfopristin, quinupristin, azithromycin, clarithromycin, erythromycin, roxithromycin, linezolid, doxycycline, minocycline, tetracycline, oxytetracycline, tigecycline, norfloxacin, enoxacin, ciprofloxacin, ofloxacin, levofloxacin, moxifloxacin, metronidazole, tinidazole, aminocumarine, sulfadiazine, sulfadoxin, sulfamethoxazole, sulfasalazine, pyrimethamine, trimethoprim, rifampicin.

Anti-infective agents is a generic term for compounds that are useful in the treatment of bacterial, viral, fungal, protozoal and worm infections and comprises antibiotics, antiviral agents, antimycotics agents, antiprotozoal and anthelminthic agents.

Suitable examples for such antiplatelet agents comprise abciximab, acetylsalicylic acid, dipyridamole, clopidogrel, eptifibatide, ilomedin, prostacyclin, prasugrel, ticagrelor, ticlopidine and tirofiban.

Suitable examples for such muscle relaxants comprise tercuronium, 1-ethylcarbamoyl-3-(3-trifluoromethylphenyl) pyrrolidine, metaxalone, methocarbamol, meprobamate, baclofen, carisoprodol, chlorzoxanzone, cyclobenzaprine, dantrolene, diazepam, orphenadrine, quinine, rocuronium, succinylcholine, decamethonium, pancuronium, veruronium, rapacuronium, dacuronium, duador, malouetine, dipyrandium, pipercuronium, chandonium, HS-342, atracurium, mivacurium, doxacurium, d-tubocurarine, dimethyltubocurarine, gallamine, alcuronium, anatruxonium, diadonium, fazadinium, tropeinium, cisatrucurium.

Suitable examples for such antimycotic drugs comprise abafungin, amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, amorolfin, butenafine, nafitifine, terbinafine, anidulafungin, caspofungin, micafungin, benzoic acid, ciclopirox, flucytosine, griseofulvin, haloprogin, tolnaftate, undecylenic acid, crystal violet, balsam of Peru.

Suitable examples for such antiprotozoal drugs comprise metronidazole, tinidazole, ornidazole, atovaquone, clioquinol, chlorquinaldol, emetin, pentamidine isethionate, eflornithine, nitrofural, halofuginone, miltefosine, chloroquine, hydroxychloroquine, mepacrine, primaquine, amodiaquine, pamaquine, piperaquine, proguanil, cyclohunailembonate, quinine, mefloquine, pyrimethamine, artmether, artemisinine, artesunate, dihydroartemisinine, halofantrine, lumefantrine, sulfadoxine.

Suitable examples for such anthelmintics comprise mebendazole, praziquantel, albendazole, diethylcarbamazine, flubendazole, ivermectin, levamisole, metrifonate, niclosamide, oxyclozanide, oxamniquine, oxantel, piperazine, pyrantel, pyrantel pamoate, monopantel, derquantel, pelletierine sulphate, pyrvinium, thiabendazole, fenbendazole, triclabendazole, abamectin, suramine, emodepside, pyrvinium embonate, aminoacetonitrile.

Suitable examples for such local anesthetics comprise lidocaine, lignocaine, menthol, articaine, bupivacaine, ropivacaine, benzocaine, chloroprocaine, cocaine, cyclomethycaine, dimetociane, larocaine, piperocaine, propoxycaine, procaine, novocaine, proparacaine, tetracaine, amethocaine, cinchocaine, dibucaine, etidocaine, levobupivacaine, meplavacaine, prilocaine, trimecaine, saxitoxin, neosaxitoxin, tetrodotoxin, eugenol.

Suitable examples for analgesics comprise the NSAIDs listed above; opioid analgesics such as morphine, fentanyl, methadone, oxycodon, carfetanyl, dihydroetorphin, ohmefentanyl, etorphin, sufentanil, remifentanil, alfentanil, buprenorphine, hydromorphone, levomethadone, hydrocodone, pintramide, nalbuphine, tapentadol, pentazocin, dihydrocodeine, codeine, pethidine, tramadol, tilidine, meptazinol, naloxone, naltrexone, diprenorphine, loperamide, apomorphine; epibatidine; scopolamine; ziconitide; cannabinoids such as tetrahydrocannabinol, cannabidiol, marinol; flupirtine; ketamine and local anesthetics listed above.

Suitable examples for such anticoagulants comprise heparins, coumarins such as phenprocoumon (marcumar) and warfarin, apixaban, rivaroxaban, edoxaban, dabigatran, ximelagatran, hirudine, lepirudine, bivalirudine, citrate, EDTA, fondaparinux, argatroban, otamixaban.

Tonic agents is a generic term that refers to substances that invigorate, tone or restore the body and its physiological functions. They may be of herbal or animal origin.

5-amino-2,3-dihydro-1,4-phthalazinedione or a related compound and the further active ingredient can be used simultaneously, separately or sequentially in order to treat or prevent the disease symptoms. The two active agents may be provided in a single dosage form or as separate formulation, each formulation containing at least one of the two active agents. One or both of the two active agents may be formulated as a bolus.

Any suitable route of administration for 5-amino-2,3-dihydro-1,4-phthalazinedione or a related compound may be employed for providing a subject, in particular a mammal, especially a human with an effective dosage of 5-amino-2,3-dihydro-1,4-phthalazinedione or a related compound.

According to the invention 5-amino-2,3-dihydro-1,4-phthalazinedione or a related compound, a composition containing 5-amino-2,3-dihydro-1,4-phthalazinedione or a related compound or a composition containing 5-amino-2,3-dihydro-1,4-phthalazinedione or a related compound and at least one of the aforementioned combinational drugs for use in the treatment of PPMS or SPMS can be applied orally, parenterally, intravenously, intraarterially, intramuscularly, topically, transdermally, subcutaneously, intradermally, sublingually, intravaginally, rectally or nasally.

According to the invention 5-amino-2,3-dihydro-1,4-phthalazinedione or a related compound, a composition containing said active substance or a composition containing said active substance and at least one of the aforementioned combinational drugs for use in the treatment of PPMS or SPMS can be applied simultaneously with, separately from or sequentially to complementary therapies used in the treatment of multiple sclerosis selected from a group comprising physiological exercises; physical and occupational therapy; psychological and social guidance; psychiatric and neuropsychological treatment; orthopedic, ophthalmologic and urologic care, diet and nutrition plans; and mind-body therapies such as yoga and relaxation.

In one embodiment of the invention the active ingredient is administered to a subject in need thereof wherein said subject shows at least one symptom, preferably two symptoms, most preferably three or more symptoms typical for PPMS, selected from a group comprising gradually increasing imbalance; extremity weakness; tightness, numbness and/or tingling of limbs and/or lower trunk; changes in bowel, bladder and/or sexual function; wherein said subject is preferably between 30 and 70 years of age, preferably between 40 and 60 years of age, most preferably between 40 and 50 years of age.

In a further embodiment of the invention the active ingredient is administered to a subject in need thereof showing one or more symptoms typical for PPMS as outlined above, wherein cerebrospinal fluid (CSF) of said subject shows mild inflammation with or without the presence of oligoclonal bands, preferably without the presence of oligoclonal bands.

In a further embodiment of the invention the active ingredient is administered to a subject in need thereof showing one or more symptoms typical for PPMS as outlined above, wherein cerebrospinal fluid (CSF) of said subject shows low grade inflammation in the central nervous system characterized by increased levels of either CCL4 or CXCL10, preferably both CCL4 or CXCL10 are increased.

In one embodiment of the invention the active ingredient is administered to a subject in need thereof, wherein the subject formerly diagnosed with RRMS develops a continuous deterioration of clinical symptoms and wherein latest relapse occurred at least 3 months, preferably 6 months ago.

The present patent application also refers to a method of treatment by using a 5-amino-2,3-dihydro-1,4-phthalazinedione or a related compound for the treatment of chronic progressive forms of multiple sclerosis such as PPMS and SPMS in a subject in need thereof. The method comprises the following steps: Providing a substance of the invention, a composition of the invention or a combination of the invention; and administering said substance, composition or combination in an effective amount to said subject.

The present patent application also refers to a method of treatment as described above characterized by the use of 5-amino-2,3-dihydro-1,4-phthalazinedione or a related compound according to any of the treatment regimens provided with this application.

EXAMPLES

1—MOG-Induced Experimental Autoimmune Encephalomyelitis in C57616 Mice

Background:

Experimental autoimmune encephalomyelitis (EAE) originally also referred to as experimental allergic encephalomyelitis is an animal model of immunoinflammatory disease of the CNS with clinical, histological and immunological characteristics comparable to human multiple sclerosis. EAE is thus an inflammatory disease of the CNS in rodents induced by injecting a protein which causes an immune reaction. This inducible demyelinating disease shows wide similarities with human multiple sclerosis with regard to clinical, histological and immunological characteristics. This model is broadly accepted to test the comparative efficacy of pharmaceutical agents. It shows a good predictive power for their efficacy in humans. There are several varieties of this model, depending on the mouse strain and the inflammation-stimulating protein. Some varieties are particularly predictive for specific MS disease courses. Herein the MOG-EAE model was used in C57BL6/J mice. Induced by the peptide pMOG35-55 EAE develops as primary-progressive Form in C571316 mice. Thus, this model is regarded as predictive for chronic progressive MS forms, in particular for PPMS.

Myelin oligodendrocyte glycoprotein (pMOG35-55)—in the following referred to as MOG—is applied by subcutaneous injection. MOG is a myelin-derived protein. Its extracellular immunoglobulin-like domain is expressed on the cell membrane of oligodendrocytes (Delarasse et al., 2013, Immunology 140(4): pp. 456-464). Within two weeks after immunization with an emulsion comprising MOG and complete Freund adjuvant (CFA) and challenge with pertussis toxin, peripheral immune responses are initiated that subsequently cause inflammation in the CNS. Thereafter, zones of demyelination can be seen in association with perivascular inflammation, cell infiltrates and progressively ascending paralysis. EAE induced by the MOG develops as primary-progressive form in H2bmice (i.e. C57BL6/J) and as progressive relapsing clinical Form in H2Umice (Kerlero de Rosbo et al., 1995, Eur J Immunol 25, pp. 985-993; Mendel et al., 1995, Eur J Immunol 25, pp. 1951-1959).

Three different MOG-EAE experiments are described in the following. Induction and Scoring was performed in the same way in all three experiments:

Induction:

Mice were immunized by s.c. injection of an emulsion composed of 200 μg $MOG_{35-55}$ peptide (Genemed Synthesis, San Francisco, Calif.) in Complete Freund's Adjuvant (CFA, Difco, Detroit, U.S.A.) containing 0.5 mg (per injection) of *Mycobacterium tuberculosis*. Each mouse received subcutaneous injections of 200 μl emulsion equally divided among two sites, left and right flank, draining into the axillary lymph nodes. Pertussis toxin (Calbiochem, Nottingham, UK) was used as a co-adjuvant and was administered i.p. at the dose of 200 ng/mouse on clay 0 and 200 ng/mouse on day 2 post immunization.

Due to quality aspects mice considered as SHAM were injected with Freund adjuvant only. They are not further mentioned in the following.

Scoring:

Starting from day 7 post-immunization the animals were examined individually for the presence of paralysis according to the following score: 0=no sign of disease; 0.5=partial tail paralysis; 1=tail paralysis; 1.5=tail paralysis+partial unilateral hind limb paralysis; 2=tail paralysis+hindlimb weakness or partial hindlimb paralysis; 2.5=tail paralysis+partial hindlimb paralysis (lowered pelvis); 3=tail paralysis+complete hindlimb paralysis; 3.5=tail paralysis+complete hindlimb paralysis+incontinence; 4=tail paralysis+hindlimb paralysis+weakness or partial paralysis of forelimbs; 5=moribund or dead.

The following parameters have been investigated in all three experiments: A cumulative score was calculated for each mouse by adding the daily scores from the day of onset (score disease≥0.5) until the end of treatment. A maximal score was assessed by taking the highest score reached throughout the experiment for each animal. The disease incidence was determined by summing up the number of animals per group that ever showed a score z 0.5. This parameter showed that the MOG-EAE model worked well in all three experiments. Disease duration was calculated by assigning each day a score of 0 and 1 for any clinical score higher than 0 for each animal. Disease onset was determined by taking the first day an animal showed a score z 0.5. Animals that never showed any symptoms were not evaluated.

Observation of the animals took place in a quiet room. Clinical signs were monitored daily and body weight was monitored three times a week in each group of treatment in a blinded fashion. Animals reaching a score of 3 were monitored closely and supportive care was initiated, if necessary. To these animals, soft food was offered to encourage feed intake and the loss of fluids and minerals was balanced by respective subcutaneous injections. Mice reaching a score of 4 were ethically euthanized. Also, animals with more than 20% body weight loss and/or animals experiencing severe pain or suffering were euthanized regardless of the clinical score. The substance used in these experiments is according to 5-amino-2,3-dihydro-1,4-phthalazinedione sodium salt polymorphic Form I (from Applicant's GMP production) as described in WO 2011/107295 and will be referred to as Form I in the following. Form I has been described as predominantly immunostimulatory compared to the predominantly immunosuppressive effect of form II also described in WO2011/107295A1. However, both of these forms have been described as immune modulating. But, when it comes to effects on neurodegenerative lesions both forms have to be regarded as equally. Although slight differences in bioavailability and pharmacokinetics might occur between these two forms when provided in specific formulations, the qualitative effect of both forms is the same. Dexamethasone (Soldesam®) was used as positive control drug. In all experiments the intraperitoneal treatment with the test compound appeared to be well tolerated as judged by clinical status of the mice and by body weight variation similar to vehicle-treated mice. There were no significant body weight changes throughout the groups during the whole study.

A—Late Prophylactic Effects (I)

Study design: Five groups of 10 animals each were treated with 5-amino-2,3-dihydro-1,4-phthalazinedione sodium salt for 40 consecutive days under a late prophylactic regime starting day 7 after immunization with intraperitoneal injections once daily, as described in the table below.

| Group | Treatment | Daily dose |
| --- | --- | --- |
| 1 | Form I | 0.5 mg/kg |
| 2 | Form I | 1.5 mg/kg |
| 3 | Form I | 4.5 mg/kg |
| 4 | dexamethasone | 0.3 mg/kg |
| 5 | vehicle | — |

One animal from the group dosed with 0.5 mg/kg Form I died on Day 1 (no score assessed). Another animal treated with 4.5 mg/kg Form I died on Day 21 (Score 1.5 at that timepoint). Thus, for statistical evaluation, the number of animals was slightly reduced. Both mice died independent of treatment, the score hitherto was not evaluated. The doses of the compounds were chosen based on previous chronic animal models with Form I.

Results:

The MOG-EAE model worked well. Classical signs of EAE started to appear in the vehicle-treated control animals 13 days after immunization. The late prophylactic treatment with Form I showed a dose-dependent effect in the course of the disease with a Form I concentration of 0.5 mg/kg, 1.5 mg/kg and 4.5 mg/kg, compared to vehicle-treated mice. The effects with 4.5 mg/kg were superimposable to those observed with dexamethasone. The course of the average clinical score per group over time is depicted in FIG. 1.

Figure 2:
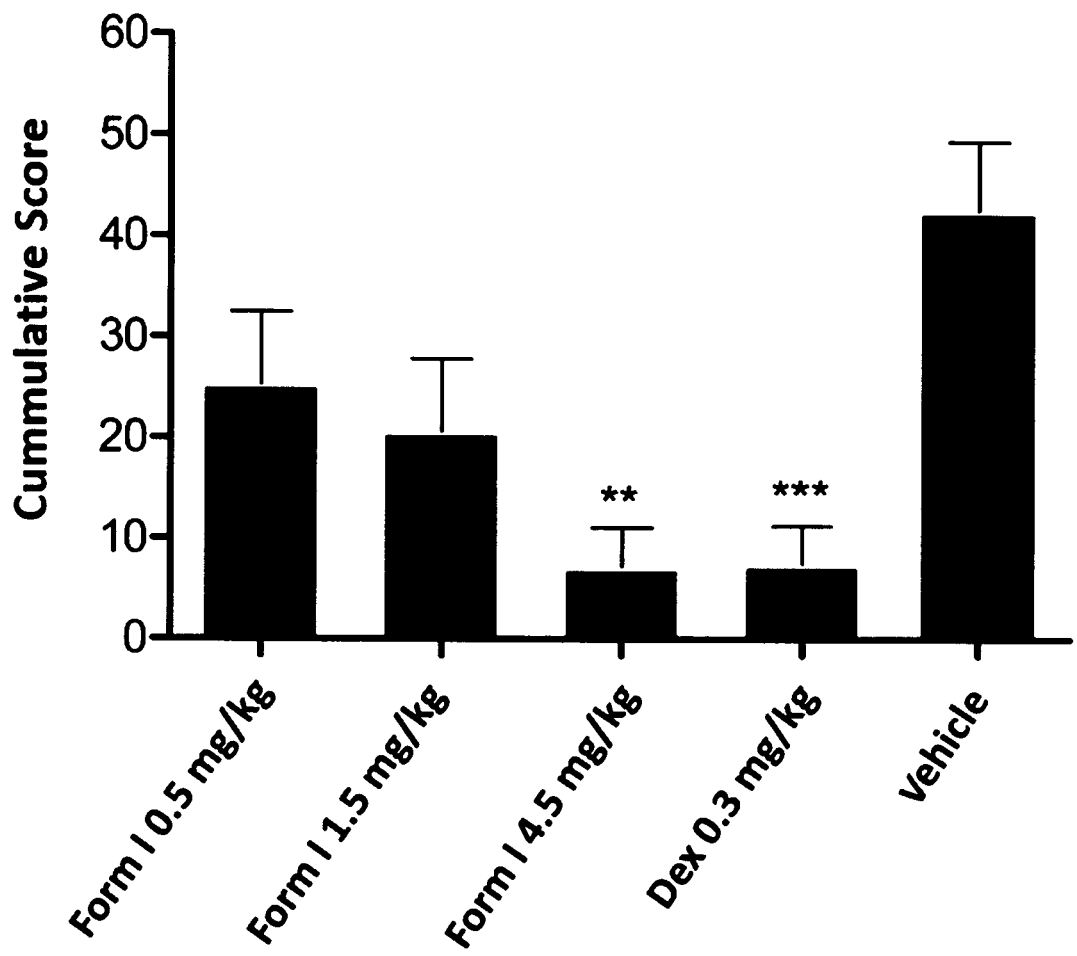

The evaluation of the cumulative score shows a dose-dependent reduction of the score with increased concentrations of Form I exhibiting a significant reduction of the score by 4.5 mg/kg Form I compared to vehicle-treated mice. Dexamethasone also significantly reduced the cumulative score. FIG. 2 summarizes the cumulative scores per group.

As expected, the highest scores were reached in the vehicle group. The concentration of 4.5 mg/kg Form I shows a significant reduction of the maximal score compared to vehicle-treated mice. With dexamethasone it was also significantly reduced, whereas Form I in a concentration of 0.5 mg/kg and 1.5 mg/kg causes only a slight reduction of the maximal disease manifestation, compared to vehicle-treated mice (data not shown).

Concerning disease incidences a dose-dependent effect of Form I was detected. Mice treated with Form I concentrations of 0.5 or 1.5 mg/kg show a lesser incidence than vehicle-treated mice. A clearly reduced incidence could be observed in the groups treated with dexamethasone or 4.5 mg/kg Form I (data not shown).

The late prophylactic treatment with Form I showed a dose-dependent effect on the disease duration, reaching a statistically significant effect with the dose of 4.5 mg/kg MP 1032 compared to vehicle. Also, dexamethasone significantly reduces the disease duration (data not shown). Disease onset was significantly later in the groups with 4.5 mg/kg Form I and dexamethasone, compared to vehicle-treated mice. There was a dose-dependency in the disease onset in Form I-treated mice (data not shown).

B—Late Prophylactic Effects (II)

Study Design:

As the administration of 4.5 mg/kg Form I proved (Example A) to be the most effective the experiment was repeated with 10 further animals receiving 4.5 mg/kg Form I compared to two groups of 6 animals each being administered Vehicle and Dex. The late prophylactic regimen started on day 7 after immunization, via once daily i.p. injections for 43 consecutive days.

| Group | Treatment | Daily dose |
| --- | --- | --- |
| 1 | Form I | 4.5 mg/kg |
| 2 | dexamethasone | 0.3 mg/kg |
| 3 | vehicle | — |

For statistical evaluation the number of animals was slightly reduced as two animals from the group dosed with 4.5 mg/kg Form I and one animal of the dexamethasone group died before the treatment started. Hence, all three mice died independent of treatment, the score hitherto was not evaluated.

Figure 3:
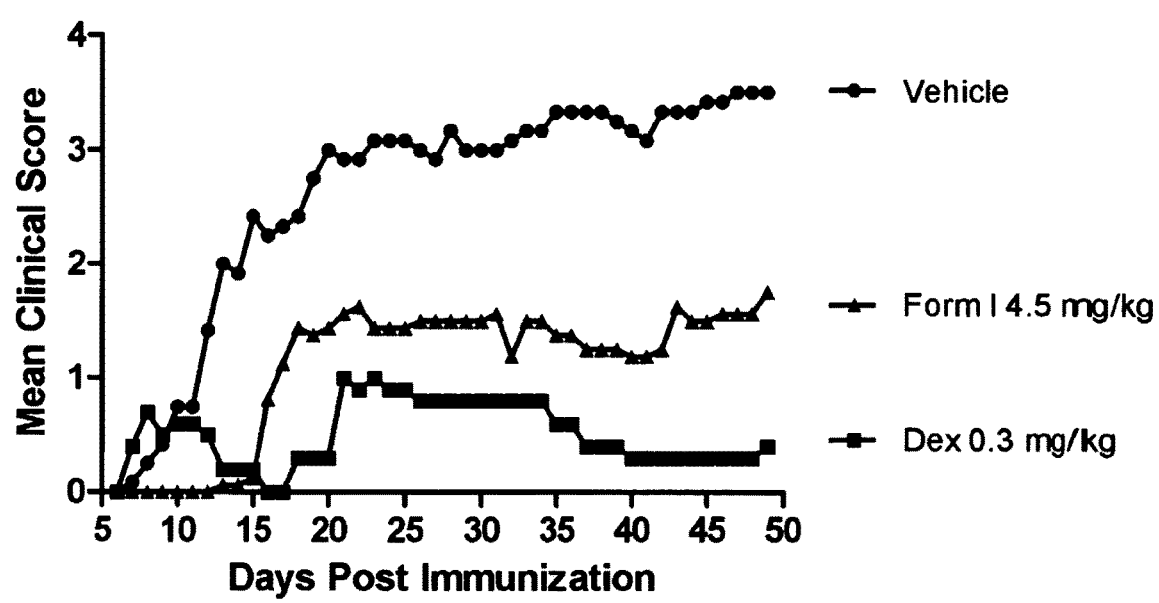

Results:

The MOG-EAE model worked well, although the clinical course was more aggressive compared to the first study (A). Classical signs of EAE already started to appear in the vehicle-treated control animals 7 days after immunization. For the late prophylactic treatment with 4.5 mg/kg Form I the results of the first study (A) could be confirmed. This treatment lead to a significant amelioration of the clinical course compared to vehicle-treated mice. The course of the average clinical score per group over time is depicted in FIG. 3.

Figure 4:
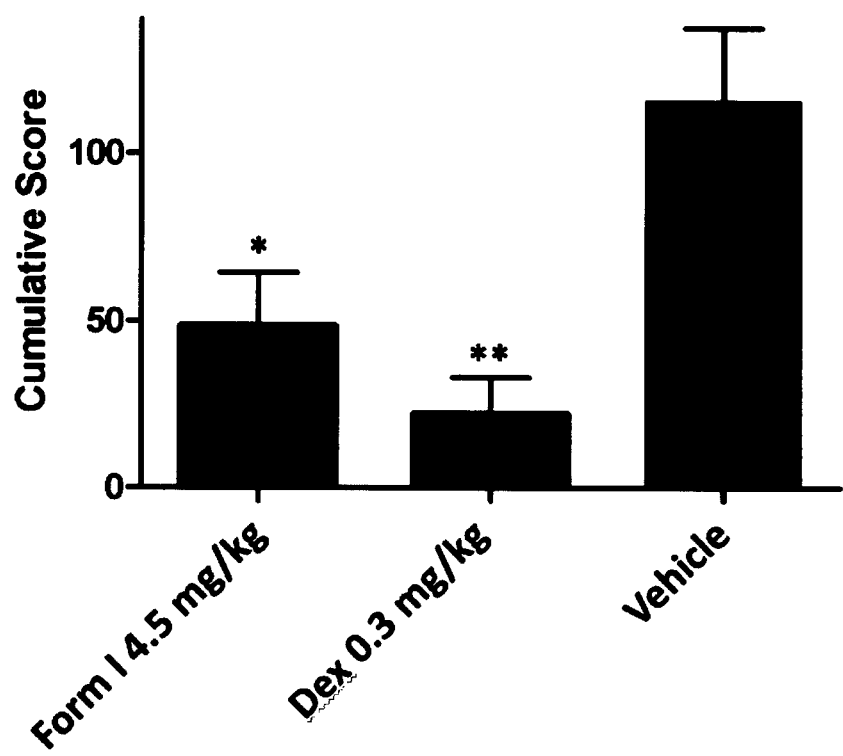

A cumulative score was calculated for each mouse by adding the daily scores from the day of onset (score disease≥0.5) until the end of treatment. The evaluation of the cumulative score showed a statistically significant reduction of the score in the 4.5 mg/kg Form I group compared to vehicle group. Dexamethasone also significantly reduced the cumulative score. FIG. 4 summarizes the cumulative scores per group.

Again, the highest scores were reached in the vehicle group and the group with 4.5 mg/kg Form I showed a trend towards reduction of the maximal score compared to vehicle-treated mice. With dexamethasone it was significantly reduced (data not shown).

No statistically significant differences between groups could be shown for disease incidence. The late prophylactic treatment with Form I showed a statistically significant reduction of disease duration compared to vehicle. Also, dexamethasone significantly reduced the disease duration (data not shown).

Disease onset was not significantly later in the groups treated with 4.5 mg/kg Form I and dexamethasone, compared to vehicle-treated mice.

C—Therapeutic Effects

Study Design:

The most effective dose of Form I (4.5 mg/kg) as found in Example A has also been investigated in 10 animals in a therapeutic model. Two groups of 6 animals each were used for vehicle and dexamethasone. The animals in the therapeutic regimen received once daily i.p. injections for 30 consecutive days, starting from the first day with a clinical score equal to or greater than 0.5.

| Group | Treatment | Daily dose |
|---|---|---|
| 1 | Form I | 4.5 mg/kg |
| 2 | dexamethasone | 0.3 mg/kg |
| 3 | vehicle | — |

The doses of the compounds were chosen based on the previously performed EAE model (A). For statistical evaluation the number of animals was slightly reduced as two animals from the group dosed with 0.3 mg/kg dexamethasone and one animal from the group dosed with 4.5 mg/kg Form I died before the treatment started. Hence, all three mice died independent of treatment, the score hitherto was not evaluated. Further two animals from the group dosed with 4.5 mg/kg Form I didn't develop disease and were thus neither dosed nor statistically evaluated.

Results:

The MOG-EAE model worked well, although the clinical course was more aggressive compared to the first study (A). Classical signs of EAE already started to appear in the vehicle-treated control animals 7 days after immunization.

Figure 5:
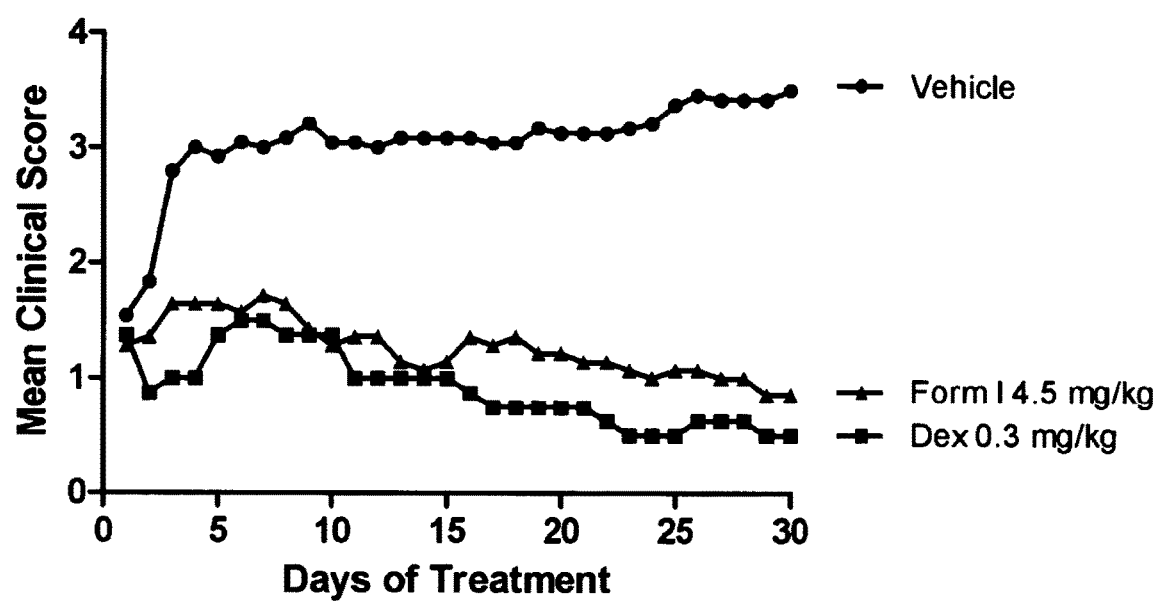
Figure 6:
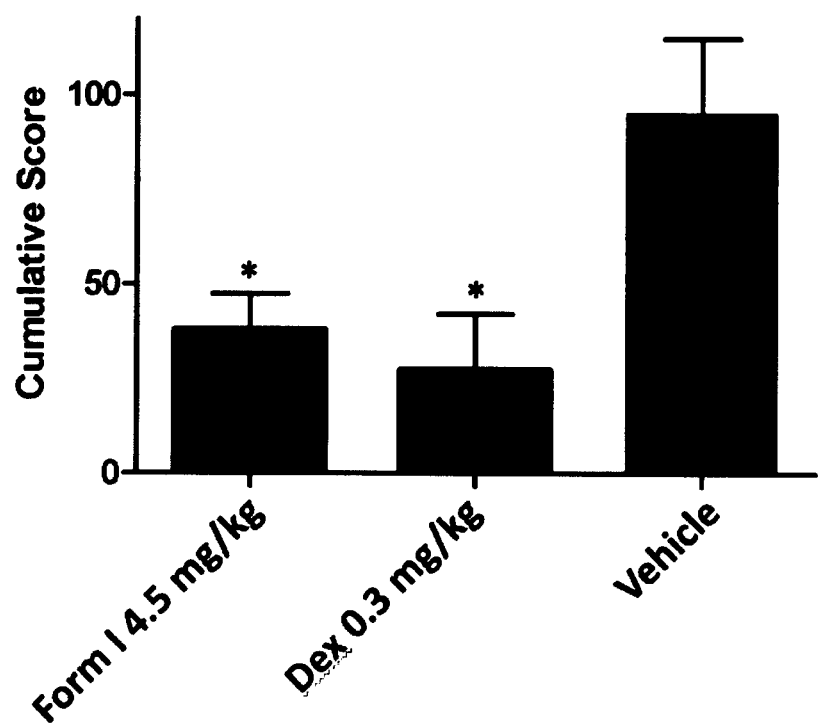

Also for the therapeutic treatment 4.5 mg/kg Form I turned out as a good option as this treatment lead to a statistically significant amelioration of the clinical course compared to vehicle-treated mice. The course of the average clinical score per group over time is depicted in FIG. 5. A cumulative score was calculated for each mouse by adding the daily scores from the day of onset (score disease≥0.5) until the end of treatment. The evaluation of the cumulative score showed a statistically significant reduction of the score in the 4.5 mg/kg Form I group compared to vehicle group. Dexamethasone also significantly reduced the cumulative score. FIG. 6 summarizes the cumulative scores per group.

Figure 7:
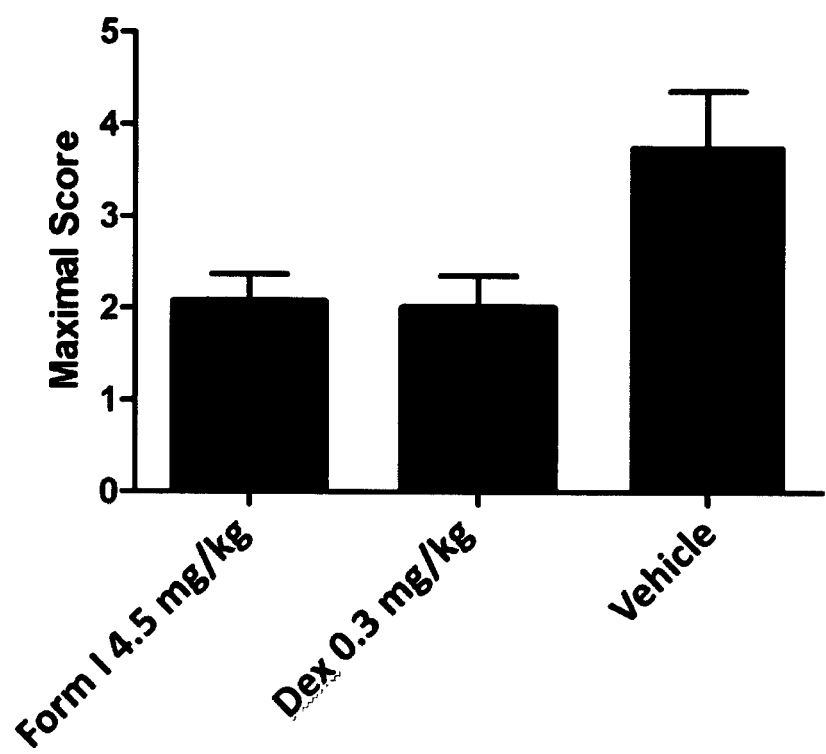

The group being administered 4.5 mg/kg Form I showed a clear but statistically not significant reduction of the maximal score compared to vehicle-treated mice. The same result was found for dexamethasone (FIG. 7).

No statistically significant differences between groups could be shown for disease incidence.

The therapeutic treatment with Form I showed a trend towards reduction of disease duration compared to vehicle. Dexamethasone significantly reduced the disease.

Disease onset was not significantly later in the groups treated with 4.5 mg/kg Form I and dexamethasone, compared to vehicle-treated mice.

2—Adjuvant Induced Arthritis in Lewis Rats (Reference Example):

Form I has earlier been tested in adjuvant induced arthritis (AIA) in Lewis rats, an animal model mirroring human rheumatoid arthritis (Kannan et al., 2005, Pathophysiology 12, pp. 167-181). The disease can be induced in Lewis rats by a single intracutaneous inoculation of killed mycobacteria suspended in CFA. Form I was administered i.p. at the dose of 0.5, 1 and 5 mg/kg daily for 3 weeks as a late prophylactic treatment starting on day 7 after immunization. A vehicle group was used as negative control and dexamethasone (0.3 mg/kg) as positive control. Rats were evaluated for arthritis daily by an observer unaware of the treatment according to a macroscopic scoring system. An arthritis index was calculated for each rat by summing the scores for the individual paws. Relative to vehicle-treated rats, the treatment with the low dose of Form I (0.5 mg/kg) significantly reduced the arthritic score of the disease starting from day 26 to 37, the medium dose (1 mg/kg) from 19 to 37 and higher dose (5 mg/kg) only on day 33. The most effective dose was the medium that was also able to reduce significantly the cumulative score of the disease compared to vehicles (data not shown).

3—Cytokine Levels after Administration of a Sublethal Dose of LPS in CD1 Mice (Reference Example):

5-amino-2,3-dihydro-1,4-phthalazinedione sodium salt polymorphic Form II as described in WO 2011/107295 will be referred to as Form II in the following. Form II has earlier been tested for its effects on circulating levels of TNF-alpha and IL-6 2 and 4 hours after administration of a sublethal dose of LPS in CD1 mice. Therefore, Form II was administered i.p. at the dose of 0.5, 1.5 and 15.0 mg/kg 15 minutes before LPS challenge. A vehicle group was used as negative control and dexamethasone (0.3 mg/kg) as positive control. Form II significantly reduced the blood levels of inflammatory cytokines provoked by injection with a sublethal dose of LPS. Significant results were available for TNF-alpha after 2 hours and for IL-6 after 2 and after 4 hours. The dose of 0.5 mg/kg showed the best efficacy in down-regulation of both TNF-alpha and IL-6. Downregulation of TNF-alpha was significant compared to vehicle in the Form II doses of 0.5 mg/kg and 1.5 mg/kg, but not for 15 mg/kg. Downregulation of IL-6 was significant compared to vehicle in the Form II doses of 0.5 mg/kg, but not for 1.5 mg/kg and 15 mg/kg (data not shown).

In a second experiment the effective dosage of 0.5 mg/kg i.p. was confirmed for Form I as well. Additionally, it was shown that there was an effect when Form I was applied orally as well (data not shown).

4—Treatment Regimens:

A patient with suspected or freshly diagnosed PPMS or SPMS and a EDSS 4.0 may be administered 200 mg of 5-amino-2,3-dihydro-1,4-phthalazinedione sodium salt twice a day. EDSS determination is then performed every 6 months. First EDSS change is seen after 18 months as an increase of 0.5 points. Thus, the dosage is increased to 300 mg twice a day. A second EDSS change is seen 6 months after dosage adjustment, EDSS is back at 4.0. 36 months after dosage adjustment EDSS is again at 4.5. No dosage adjustment is necessary. Five years (60 months) after start of treatment the patient shows a disability progression of 0.5 EDSS points. If the patient stays untreated a progression of approximately 1.5 to 2.0 has to be expected. Another patient with formerly diagnosed PPMS or SPMS and a EDSS 5.0 may depending on the cruise of EDSS progression optionally be administered a parenteral bolus of 600 mg 5-amino-2,3-dihydro-1,4-phthalazinedione sodium salt applied intravenously before the following treatment regime start. The patient may then be administered 300 mg of 5-amino-2,3-dihydro-1,4-phthalazinedione sodium salt twice a day over a period of 2 weeks, subsequently followed by the administration of 200 mg once daily over a period of 6 weeks. Then for the next 4 weeks the active substance is not administered before the next treatment round starts. The next treatment round might vary in dosages used and duration of the treatments depending on disease progression.

SHORT DESCRIPTION OF THE FIGURES

In all figure legends Form I refers to the aforementioned Form I of 5-amino-2,3-dihydro-1,4-phthalazinedione sodium salt and Dex to dexamethasone.

FIG. 1 shows the course of the average clinical disability score per group over time in a late prophylactic MOG-EAE mouse model (Example 1A).

FIG. 2 shows a cumulative score (mean+SEM) which was calculated for each mouse by adding the daily scores from the day of onset (score disease z 0.5) until the end of treatment in a late prophylactic MOG-EAE mouse model (Example 1A). A two-tailed Mann-Whitney test has been performed. Statistical significance is displayed as follows $p<0.001=*$; $p=0.001$ to $<0.01=$, $p=0.01$ to $0.05=*$; compared to vehicle.

FIG. 3 shows the course of the average clinical disability score per group over time in a late prophylactic MOG-EAE mouse model (Example 1B).

FIG. 4 shows a cumulative score (mean+SEM) which was calculated for each mouse by adding the daily scores from the day of onset (score disease z 0.5) until the end of treatment in a late prophylactic MOG-EAE mouse model (Example 1B). A two-tailed Mann-Whitney test has been performed. Statistical significance is displayed as follows $p<0.001=*$; $p=0.001$ to $<0.01=$, $p=0.01$ to $0.05=*$; compared to vehicle.

FIG. 5 shows the course of the average clinical disability score per group over time in a therapeutic MOG-EAE mouse model (Example 1C).

FIG. 6 shows a cumulative score (mean+SEM) which was calculated for each mouse by adding the daily scores from the day of onset (score disease z 0.5) until the end of treatment in a therapeutic MOG-EAE mouse model (Example 1C). A two-tailed Mann-Whitney test has been performed. Statistical significance is displayed as follows $p<0.001=*$; $p=0.001$ to $<0.01=$, $p=0.01$ to $0.05=*$; compared to vehicle.

FIG. 7 shows the maximal score (mean+SEM), i.e. the symptom peak which was determined by taking the highest score reached throughout the experiment for each mouse in a therapeutic MOG-EAE mouse model (Example 1C). A two-tailed Mann-Whitney test has been performed. Statistical significance is displayed as follows $p<0.001=*$; $p=0.001$ to $<0.01=$, $p=0.01$ to $0.05=*$; compared to vehicle.

The invention claimed is:

1. A method of treating an individual having a chronic progressive form of multiple sclerosis by administering to such individual a pharmaceutically effective amount of 5-amino-2,3-dihydro-1,4-phthalazinedione, or one of its solvates, hydrates, crystalline polymorphs, tautomers, isotopically enriched forms, or one of their pharmaceutically acceptable salts.

2. The method of claim 1, wherein said pharmaceutically acceptable salt is a 5-amino-2,3-dihydro-1,4-phthalazinedione sodium salt.

3. The method of claim 2, wherein said substance is a crystalline polymorph of 5-amino-2,3-dihydro-1,4-phthalazinedione sodium salt selected from a group comprising Form I, Form II and Form III, wherein said Form I, Form II and Form III, respectively, are characterized by the following crystallography values determined by means of x-ray powder diagrams:

Form I:
d values: 13.5; 6.9; 5.2; 4.6; 3.9; 3.5; 3.4; 3.3; 3.1; 3.0 and/or
2-theta values: 6.5; 12.7; 16.9; 19.3; 22.8; 25.8; 26.6; 27.2; 28.7; 30.3;

Form II:
d values: 12.9; 7.9; 7.1; 6.5; 5.3; 4.0; 3.7; 3.6; 3.3; 3.2 and/or
2-theta values: 6.8; 11.2; 12.5; 13.7; 16.7; 22.4; 24.3; 24.9; 27.2; 27.8;

Form III:
d values: 13.131; 7.987; 7.186; 6.566; 6.512; 5.372; 3.994; 3.662; 3.406; 3.288; 3.283; 3.222; 3.215; 3.127; 2.889 and/or
2-theta values: 6.73; 11.07; 12.31; 13.48; 13.59; 16.49; 22.24; 24.29; 26.14; 27.10; 27.14; 27.67; 27.72; 28.52; 30.93.

4. The method of claim 1, wherein said chronic progressive form of multiple sclerosis is primary progressive multiple sclerosis.

5. The method of claim 1, wherein said chronic progressive form of multiple sclerosis is secondary progressive multiple sclerosis.

6. The method of claim 1, wherein 5-amino-2,3-dihydro-1,4-phthalazinedione or one of its solvates, hydrates, crystalline polymorphs, tautomers, isotopically enriched forms, or one of their pharmaceutically acceptable salts is used in a combinational therapy together with at least one drug used in disease modifying or symptomatic therapies for multiple sclerosis, wherein said at least one drug is selected from a group comprising beta interferons, glatiramer acetate, fingolimod, teriflunomid, mitoxantrone, natalizumab, laquinimod, dimethyl fumarate, alemtuzumab, idebenone, ibudilast, ocrelizumab, methylprednisolone, cyclophosphamide, piracetam, pyridoxine hydrochloride, vitamin D, gabapentin, carbamazepine, pregabalin, oxcarbazepine, clonazepam, baclofen, tizanidine, localized botulinum toxin injections, propranolol, primidone, modafinil, armodafinil, methylphenidate, fampridine, dalfampridine, amantadine, solifenacin, darifenacin, tolterodine, fesoterodine, trospium and oxybutynin.

7. The method of claim 1, wherein 5-amino-2,3-dihydro-1,4-phthalazinedione or one of its solvates, hydrates, crystalline polymorphs, tautomers, isotopically enriched forms, or one of their pharmaceutically acceptable salts is used as a monotherapy.

8. The method of claim 1, wherein 5-amino-2,3-dihydro-1,4-phthalazinedione or one of its solvates, hydrates, crystalline polymorphs, tautomers, isotopically enriched forms, or one of their pharmaceutically acceptable salts is applied orally.

9. The method of claim 1, wherein 5-amino-2,3-dihydro-1,4-phthalazinedione or one of its solvates, hydrates, crystalline polymorphs, tautomers, isotopically enriched forms, or one of their pharmaceutically acceptable salts is administered over at least two weeks using a daily dosage between 50 mg and 1200 mg.

10. The method of claim 1, wherein the administration of and effective dosage of 5-amino-2,3-dihydro-1,4-phthalazinedione or one of its solvates, hydrates, crystalline polymorphs, tautomers, isotopically enriched forms, or one of their pharmaceutically acceptable salts to said individual is regularly adapted based on disability progression as determined by EDSS scale, wherein said substance is administered one or more times daily over at least 12 months using an effective dosage between 200 mg and 600 mg daily prior to first dosage adaption.

11. The method of claim 1, wherein 5-amino-2,3-dihydro-1,4-phthalazinedione or one of its solvates, hydrates, crystalline polymorphs, tautomers, isotopically enriched forms, or one of their pharmaceutically acceptable salts is administered to an individual showing at least one symptom typical for primary progressive multiple sclerosis, selected from a group comprising gradually increasing imbalance; extremity weakness; tightness, numbness or tingling of limbs or lower trunk; and changes in bowel, bladder or sexual function.

* * * * *